US007449570B2

(12) United States Patent
Wilde et al.

(10) Patent No.: US 7,449,570 B2
(45) Date of Patent: *Nov. 11, 2008

(54) USE OF NUCLEOSIDE COMPOUNDS FOR NONSENSE SUPPRESSION AND THE TREATMENT OF GENETIC DISEASES

(75) Inventors: Richard G. Wilde, Somerville, NJ (US); Neil G. Almstead, Holmdel, NJ (US); Ellen M. Welch, Califon, NJ (US); Holger Beckmann, Freiburg (DE)

(73) Assignees: PTC Therapeutics, Inc., South Plainfield, NJ (US); Amgen Inc., Thousand Oaks, CA (US)

( * ) Notice: Subject to any disclaimer, the term of this patent is extended or adjusted under 35 U.S.C. 154(b) by 82 days.

This patent is subject to a terminal disclaimer.

(21) Appl. No.: 11/048,659

(22) Filed: Jan. 21, 2005

(65) Prior Publication Data
US 2006/0166926 A1 Jul. 27, 2006

Related U.S. Application Data

(63) Continuation of application No. PCT/US03/23185, filed on Jul. 23, 2003.

(60) Provisional application No. 60/398,334, filed on Jul. 24, 2002.

(51) Int. Cl.
*A61K 31/7008* (2006.01)
*A61K 31/7028* (2006.01)
*C07H 5/04* (2006.01)
*C07H 7/06* (2006.01)

(52) U.S. Cl. .................. 536/29.11; 514/42; 514/43

(58) Field of Classification Search ............ 514/42, 514/43
See application file for complete search history.

(56) References Cited

U.S. PATENT DOCUMENTS 5,324,731 A * 6/1994 Kaddurah-Daouk et al. 514/275

OTHER PUBLICATIONS

U.S. Appl. No. 10/625,059, filed Apr. 2004, Wilde et al.*

Sanghvi et al., "Antitumor and Antiviral Activity of Synthetic alpha- and beta- Ribonucleotides of Certain Substituted Pyrimido[5,4-d]pyrimidines: A new Synthetic Strategy for Exocyclic Aminonucleosides" J. Med. Chem. (1989) vol. 32, pp. 629-637.*
Santos-Silva et al., "Killing of lymphoblastic leukemia cells by nitric oxide and taxol: involvement of NF-kB activity" Cancer Letters (2001) vol. 173, pp. 53-61.*
Grem et al., "Cytotoxicity and Metabolism of 4-Methoxy-8-(beta-D-Ribofuranosylamino)Pyrimido[5,4-d]Pyrimidine in HCT 116 Colon Cancer Cells" Biochemical Pharmacology (1994) vol. 48 No. 11, pp. 2117-2126.*
Franchetti et al., Synthesis -f 3-Deazaclitocine [2-Amino-3-Nitro-4-(beta-D-Ribofuranosylamino)pyridine] as Cytotoxic Agent Nucleosides and Nucleotides (1991) vol. 10, No. 1-3, pp. 543-545.*
Barton-Davis et al., "Aminoglycoside Antibiotics Restore Dystrophin Function to Skeletal Muscle of MDX Mice", *J. Clin. Invest.* 104:375-381 (1999).
Bedwell et al., "Suppression of a CFTR premature stop mutation in a bronchial epithelial cell line", *Nat. Med.* 3:1280-1284 (1997).
Howard et al., "Aminoglycoside antibiotics restore CFTR function by overcoming premature stop mutations", *Nat. Med.* 2:467-469 (1996).
Kamikawa et al., "Synthesis of Clitocine, a New Insecticidal Nucleoside from the Mushroom *Clitocybe inversa* ", *J. Chem. Soc. Chem. Commun.* 195 (1988).
Kubo et al, "Clitocine, a New Insecticidal Nucleoside from the Mushroom *Clitocybe inversa*", *Tet, Lett.* 27:4277 (1986).
Lee et al., "Synthesis and Biological Evaluation of Clitocine Analogues as Adenosine Kinase Inhibitors", *Bioorganic & Medicinal Chemistry Letters*, 11:2419-2422 (2001).
Moss et al., "Synthesis, Intramolecular Hydrogen Bonding, and Biochemical Studies of Clitocine, a Naturally Occuring Exocyclic Aminonucleoside", *J. Med. Chem.* 31:786-790 (1988).
Palmer et al., "Synthesis of Carbocyclic Clitocine", *Tetrahedron Letters*, 31:279-282 (1990).
Sleat et al., "Aminoglycoside-mediated suppression of nonsense mutations in late infantile neuronal ceroid lipofuscinosis", *Eur. J. Ped. Neurol.* 5:Suppl. A. pp. 57-62 (2001).

* cited by examiner

*Primary Examiner*—Shaojia Anna Jiang
*Assistant Examiner*—Eric S Olson
(74) *Attorney, Agent, or Firm*—Jones Day

(57) ABSTRACT

The invention encompasses nucleoside compounds, compositions comprising the compounds and methods for treating or preventing diseases associated with nonsense mutations of mRNA by administering these compounds or compositions.

18 Claims, No Drawings

US 7,449,570 B2

USE OF NUCLEOSIDE COMPOUNDS FOR NONSENSE SUPPRESSION AND THE TREATMENT OF GENETIC DISEASES

This application is a continuation of International Application No. PCT/US03/23185 filed Jul. 23, 2003, which claims the benefit of U.S. provisional application No. 60/398,334, filed on Jul. 24, 2002, the disclosures of which are incorporated by reference herein in their entirety.

1. FIELD OF INVENTION

The invention encompasses nucleoside compounds, compositions comprising the compounds and methods for treating or preventing diseases associated with nonsense mutations of mRNA by administering these compounds or compositions.

2. BACKGROUND OF THE INVENTION

Gene expression in cells depends upon the sequential processes of transcription and translation. Together, these processes produce a protein from the nucleotide sequence of its corresponding gene.

Transcription involves the synthesis of mRNA from DNA by RNA polymerase. Transcription begins at a promoter region of the gene and continues until termination is induced, such as by the formation of a stem-loop structure in the nascent RNA or the binding of the rho gene product.

Protein is then produced from mRNA by the process of translation, occurring on the ribosome with the aid of tRNA, tRNA synthetases and various other protein and RNA species. Translation comprises the three phases of initiation, elongation and termination Translation is initiated by the formation of an initiation complex consisting of protein factors, mRNA, tRNA, cofactors and the ribosomal subunits that recognize signals on the mRNA that direct the translation machinery to begin translation on the mRNA. Once the initiation complex is formed, growth of the polypeptide chain occurs by the repetitive addition of amino acids by the peptidyl transferase activity of the ribosome as well as tRNA and tRNA synthetases. The presence of one of the three termination codons (UAA, UAG, UGA) in the A site of the ribosome signals the polypeptide chain release factors (RFs) to bind and recognize the termination signal. Subsequently, the ester bond between the 3' nucleotide of the tRNA located in the ribosome's P site and the nascent polypeptide chain is hydrolyzed, the completed polypeptide chain is released, and the ribosome subunits are recycled for another round of translation.

Mutations of the DNA sequence in which the number of bases is altered are categorized as insertion or deletion mutations (frameshift mutations) and can result in major disruptions of the genome. Mutations of the DNA that change one base into another and result in an amino acid substition are labeled missense mutations. Base substitutions are subdivided into the classes of transitions (one purine to another purine, or one pyrimidine to another pyrimidine) and transversions (a purine to a pyrimidine, or a pyrimidine to a purine).

Transition and transversion mutations can result in a nonsense mutation changing an amino acid codon into one of the three stop codons. These premature stop codons can produce aberrant proteins in cells as a result of premature translation termination. A nonsense mutation in an essential gene can be lethal and can also result in a number of human diseases, such as, cancers, lysosomal storage disorders, the muscular dystrophies, cystic fibrosis and hemophilia, to name a few.

In bacterial and eukaryotic strains with nonsense mutations, suppression of the nonsense mutation can arise as a result of a mutation in one of the tRNA molecules so that the mutant tRNA can recognize the nonsense codon, as a result of mutations in proteins that are involved in the translation process, as a result of mutations in the ribosome (either the ribosomal RNA or ribosomal proteins), or by the addition of compounds known to alter the translation process (for example, cycloheximide or the aminoglycoside antibiotics). The result is that an amino acid will be incorporate into the polypeptide chain, at the site of the nonsense mutation and translation will not prematurely terminate at the nonsense codon. The inserted amino acid will not necessarily be identical to the original amino acid of the wild-type protein, however, many amino acid substitutions do not have a gross effect on protein structure or function. Thus, a protein produced by the suppression of a nonsense mutation would be likely to possess activity close to that of the wild-type protein. This scenario provides an opportunity to treat diseases associated with nonsense mutations by avoiding premature termination of translation through suppression of the nonsense mutation.

The ability of aminoglycoside antibiotics to promote readthrough of eukaryotic stop codons has attracted interest in these drugs as potential therapeutic agents in human diseases caused by nonsense mutations. One disease for which such a therapeutic strategy may be viable is classical late infantile neuronal ceroid lipofuscinosis (LINCL), a fatal childhood neurodegenerative disease with currently no effective treatment. Premature stop codon mutations in the gene CLN2 encoding the lysosomal tripeptidyl-peptidase 1 (TPP-I) are associated with disease in approximately half of children diagnosed with LINCL. The ability of the aminoglycoside gentamicin to restore TPP-I activity in LINCL cell lines has been examined. In one patient-derived cell line that was compound heterozygous for a commonly seen nonsense mutation (Arg208Stop) and a different rare nonsense mutation, approximately 7% of normal levels of TPP-I were maximally restored with gentamicin treatment. These results suggest that pharmacological suppression of nonsense mutations by aminoglycosides or functionally similar pharmaceuticals may have therapeutic potential in LINCL (Sleat et. al., *Eur. J. Ped. Neurol.* 5:Suppl A 57-62 (2001)).

In cultured cells having premature stop codons in the Cystic Fibrosis Transmembrane Conductance Regulator (CFTR) gene, treatment with aminoglycosides led to the production of full length CFTR (Bedwell et. al., *Nat. Med.* 3:1280-1284 (1997); Howard et. al. *Nat. Med.* 2: 467-469 (1996)). In mouse models for Duchenne muscular dystrophy, gentamicin sulfate was observed to suppress translational termination at premature stop codons resulting in full length dystrophin (Barton-Davis et. al., *J. Clin. Invest.* 104:375-381 (1999)). A small increase in the amount of full length dystrophin provided protection against contraction-induced damage in the mdx mice. The amino acid inserted at the site of the nonsense codon was not determined in these studies.

Accordingly, small molecule therapeutics or prophylactics that suppress premature translation termination by mediating the misreading of the nonsense codon would be useful for the treatment of a number of diseases. The discovery of small molecule drugs, particularly orally bioavailable drugs, can lead to the introduction of a broad spectrum of selective therapeutics or prophylactics to the public which can be used against disease caused by nonsense mutations is just beginning.

Clitocine (6-Amino-5-nitro-4-(β-D-ribo-furanosylamino) pyrimidine) is a naturally occurring exocyclic amino nucleoside that was first isolated from the mushroom *Clitocybe inversa* (Kubo et al., *Tet. Lett.* 27: 4277 (1986)). The total synthesis of clitocine has also been reported. (Moss et al., *J. Med. Chem.* 31:786-790 (1988) and Kamikawa et al., *J. Chem. Soc. Chem. Commun.* 195 (1988)). Clitocine has been reported to possess insecticidal activity and cytostatic activity against leukemia cell lines (Kubo et al., *Tet. Lett.* 27: 4277 (1986) and Moss et al., *J. Med. Chem.* 31:786-790 (1988)). However, the use of clitocine as a therapeutic for diseases associated with a nonsense mutation has not been disclosed until now. Nor has anyone reported the development of an analogue or derivative of clitocine that has utility as a therapeutic for cancer or a disease associated with a nonsense mutation.

Citation of any reference in Section 2 of this application is not an admission that the reference is prior art to the application.

3. SUMMARY OF THE INVENTION

The present invention is based in part on the discovery of small molecules that modulate premature translation termination and/or nonsense-mediated mRNA decay. The present invention encompasses compounds of formula I, compositions comprising compounds of formula I, and methods for the use of compounds of formula I. Compounds of formula I have the structure:

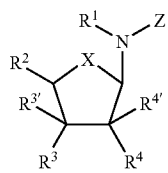

I or a pharmaceutically acceptable salt, hydrate, solvate, clathrate, racemate or stereoisomer thereof, wherein:

Z is substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, substituted or unsubstituted arylcarbonyl;

X is $CH_2$, O, S or NH;

$R^1$ is hydrogen, substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl substituted or unsubstituted cycloalkylalkyl, substituted or unsubstituted heterocycloalkyl;

$R^2$ is substituted or unsubstituted alkyl carboxy, amido, acyl, alkylcarbonyl, halogen, a biohydrolyzable group, $OP(O)_3^{2-}$, $O[P(O)_3]_2^{3-}$, $O[P(O)_3]_3^{4-}$, $N_3$, $CH_2-NR_6N_7$ or $CH_2-OR^6$;

$R^3$, $R^{3'}$, $R^4$ and $R^{4'}$ are at each occurence independently $OR^7$, $OR^8$, hydrogen, halogen, substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, substituted or unsubstituted arylcarbonyl, substituted or unsubstituted alkylcarbonyl, a biohydrolyzable group, or $R^3$ and $R^4$ taken together form a bond, or $R^3$ and $R^4$ taken together with the atoms to which they are attached form a substituted or unsubstituted heterocyclo, or $R^3$ and $R^{3'}$ and/or $R^4$ and $R^{4'}$ taken together with the carbon to which they are attached form C(=O); and $R^6$, $R^7$ and $R^8$ are at each occurrence independently hydrogen, substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, substituted or unsubstituted arylcarbonyl, substituted or unsubstituted alkylcarbonyl, a biohydrolyzable group, or $R^3$ and $R^4$ taken together with the atoms to which they are attached form a substituted or unsubstituted heterocyclo.

In another embodiment, compounds of formula I have the structure:

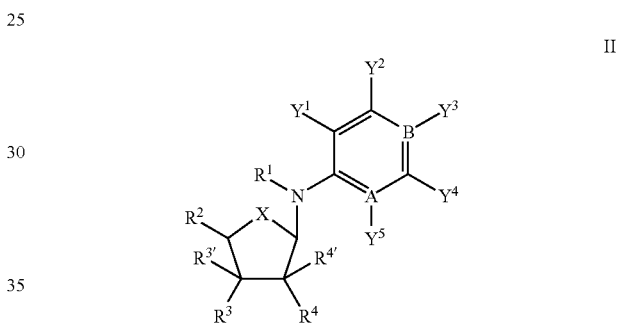

II or a pharmaceutically acceptable salt, hydrate, solvate, clathrate, racemate or stereoisomer thereof, wherein:

A and B are each independently C or N;

$Y^1$-$Y^5$ are each independently hydrogen, hydroxy, halogen, nitro, cyano, sulfate, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, alkoxy, alkylthioether, carboxyalkyl, carbonylalkyl, amino, $NR^5R^{5'}$, amido, alkylamino or alkoxycarbonyl, wherein if B is N, $Y^3$ can also be $O^-$ and if A is N, $Y^5$ can also be $O^-$, and wherein $Y^3$ is not present if B is N and $Y^5$ is not present if A is N; and $R^5$ and $R^{5'}$ are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl.

Without being limited by theory, the invention encompasses methods for modulating premature translation termination and/or nonsense-mediated mRNA decay in a cell, including mammalian cells in a living host. The invention further encompasses a method for suppressing premature translation termination and/or nonsense-mediated mRNA decay in a cell comprising contacting a cell exhibiting premature translation termination and/or nonsense-mediated mRNA decay with an effective amount of a compound of the invention. The invention further encompasses a method for inducing nonsense suppression in a cell comprising contacting a cell exhibiting a nonsense mutation with an effective amount of a compound of the invention. Accordingly, cells encompassed by the present methods include animal cells, mammalian cells, bacterial cells, plant cells and virally infected cells. In one embodiment, the nonsense mutation is a genetic mutation (i.e., the nonsense codon was present in the progenitor DNA).

Without being limited by theory, the ability of the compounds of the invention to promote readthrough of premature stop codons makes them useful in the treatment or prevention of any disease which is caused in whole or in part by a nonsense mutation. Such diseases can occur due to the decreased amount of active protein produced as a result of premature termination of translation. Without being limited by theory, the compounds of the invention allow the translation of mRNA to continue past the nonsense mutation resulting in the production of full length protein. A powerful aspect of the invention is that the therapeutic activity of compounds of the invention are not necessarily limited to a specific disease, instead are effective at treating or preventing many diseases associated with a nonsense mutation. Further, the methods of the invention include those that are patient specific, that is, a patient can be screened to determine if their disease is associated with a nonsense mutation. If so, they can then be treated with a compound of the invention more efficiently, specifically and effectively.

The compounds of the invention are useful for treating or preventing diseases associated with a nonsense mutation. Diseases that can be treated or prevented by compounds of the invention include, but are not limited to, cancer, autoimmune diseases, blood diseases, collagen diseases, diabetes, neurodegenerative diseases, cardiovascular diseases, pulmonary diseases, inflammatory diseases, lysosomal storage disease, tuberous sclerosis or central nervous system diseases.

3.1 Definitions

As used herein, "premature translation termination" refers to the result of a mutation that changes a codon corresponding to an amino acid to a stop codon.

As used herein, "nonsense-mediated mRNA decay" refers to any mechanism that mediates the decay of mRNAs containing a premature translation termination codon.

As used herein, a "premature termination codon" or "premature stop codon" refers to the occurrence of a stop codon wherein a codon corresponding to an amino acid should be.

As used herein, a "nonsense mutation" is a point mutation changing a codon corresponding to an amino acid to a stop codon. The nonsense mutation can be either a genetic mutation or a somatic mutation. A genetic mutation is one that occurs in a germ cell (i.e., wherein the nonsense codon was present in the progenitor DNA). A somatic mutation is one that occurs in the somatic tissue (i.e., non germline tissue) through mutagenesis and will not be heritable. The somatic mutation may be naturally occurring or the result of exposure to a chemical, radiation, UV rays, X-rays or other environmental factors.

As used herein, "nonsense suppression" refers to the inhibition or suppression of premature translation and/or nonsense-mediated mRNA decay.

As used herein, "modulation of premature translation termination and/or nonsense-mediated mRNA decay" refers to the regulation of gene expression by altering the level of nonsense suppression. For example, if it is desirable to increase production of a defective protein encoded by a gene with a premature stop codon, i.e., to permit readthrough of the premature stop codon of the disease gene so translation of the gene can occur, then modulation of premature translation termination and/or nonsense-mediated mRNA decay entails up-regulation of nonsense suppression. Conversely, if it is desirable to promote the degradation of an mRNA with a premature stop codon, then modulation of premature translation termination and/or nonsense-mediated mRNA decays entails down-regulation of nonsense suppression.

As used herein, the term "disease" means a condition in the patient.

As used herein, the term "patient" means an animal (e.g., cow, horse, sheep, pig, chicken, turkey, quail, cat, dog, mouse, rat, rabbit, guinea pig, etc.), preferably a mammal such as a non-primate and a primate (e.g., monkey and human), most preferably a human In certain embodiments, the patient is an infant, child, adolescent or adult. In one embodiment, it has been determined through pre-screening that the patient possesses a non-sense mutation. In another embodiment, it has been determined through pre-screening which non-sense mutation the patient has (i.e., UAA, UGA, or UAG). In another embodiment, the patient is infected with bacterial cells (e.g., *Pseudomonas aeruginosa*). In another embodiment, the cells of the patient are virally infected. In another embodiment, the patient has a genetic mutation.

As used herein, unless otherwise specified, the phrase "compound(s) of the invention" includes any compound of formula I-IX, or any compound of table 1, including any pharmaceutically acceptable salts, hydrates, polymorphs, solvates, clathrates, racemates or stereoisomers thereof. The phrase "compound(s) of the invention" also includes the a and β anomer of any compound of formula I-IX, or any compound of table 1.

As used herein, unless otherwise specified, the term "substituted" means a group substituted by one to four or more substituents, such as, alkyl, alkenyl, alkynyl, cycloalkyl, aroyl, halo, haloalkyl (e.g., trifluoromethyl), haloalkoxy (e.g., trifluoromethoxy), hydroxy, alkoxy, alkylthioether, cycloalkyloxy, heterocylooxy, oxo, alkanoyl, aryl, arylalkyl, alkylaryl, heteroaryl, heteroarylalkyl, alkylheteroaryl, heterocyclo, aryloxy, alkanoyloxy, amino, alkylamino, arylamino, arylalkylamino, cycloalkylamino, heterocycloamino, mono- and di-substituted amino (in which the two substituents on the amino group are selected from alkyl, aryl or arylalkyl), alkanoylamino, aroylamino, aralkanoylamino, substituted alkanoylamino, substituted arylamino, substituted aralkanoylamino, thiol, alkylthio, arylthio, arylalkylthio, cycloalkylthio, heterocyclothio, alkylthiono, arylthiono, arylalkylthiono, alkylsulfonyl, arylsulfonyl arylalkylsulfonyl, sulfonamido (e.g. $SO_2NH_2$), substituted sulfonamido, nitro, cyano, carboxy, carbamyl (e.g., $CONH_2$), substituted carbamyl (e.g., CONH-alkyl, CONH-aryl, CONH-arylalkyl or instances where there are two substituents on the nitrogen selected from alkyl or arylalkyl), alkoxycarbonyl, aryl, substituted aryl, guanidino, substituted or unsubstituted heterocycloalkyl, substituted or unsubstituted heteroaryl (such as, indolyl, imidazolyl, furyl, thienyl, thiazolyl, pyrrolidyl, pyridyl, pyrimidyl and the like). In one embodiment, the substituent is —O-alkyl-C(=O)-heterocyclo (substituted or unsubstituted), wherein alkyl and heterocyclo are defined above. Wherein, as noted above, the substituents themselves are further substituted, such further substituents are selected from the group consisting of halogen, alkyl, alkoxy, aryl, heteroaryl, heterocyclo, cycloalkyl, and arylalkyl.

As used herein, unless otherwise specified, the term "alkyl" means a saturated straight chain or branched non-cyclic hydrocarbon having from 1 to 20 carbon atoms, preferably 1-10 carbon atoms and most preferably 1-4 carbon atoms. Representative saturated straight chain alkyls include -methyl, -ethyl, -n-propyl, -n-butyl, -n-pentyl, -n-hexyl, -n-heptyl, -n-octyl, -n-nonyl and -n-decyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. An alkyl group can be unsubstituted or substituted. Unsaturated alkyl groups include alkenyl groups and alkynyl groups, which are discussed below.

As used herein, unless otherwise specified the term "alkenyl group" means a straight chain or branched non-cyclic hydrocarbon having from 2 to 20 carbon atoms, more preferably 2-10 carbon atoms, most preferably 2-6 carbon atoms, and including at least one carbon-carbon double bond. Representative straight chain and branched $(C_2-C_{10})$alkenyls include -vinyl, -allyl, -1-butenyl, -2-butenyl, -isobutylenyl -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like. The double bond of an alkenyl group can be unconjugated or conjugated to another unsaturated group. An alkenyl group can be unsubstituted or substituted.

As used herein, unless otherwise specified the term "alkynyl group" means a straight chain or branched non-cyclic hydrocarbon having from 2 to 20 carbon atoms, more preferably 2-10 carbon atoms, most preferably 2-6 carbon atoms, and including at lease one carbon-carbon triple bond. Representative straight chain and branched $-(C_2-C_{10})$alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like. The triple bond of an alkynyl group can be unconjugated or conjugated to another unsaturated group. An alkynyl group can be unsubstituted or substituted.

As used herein, unless otherwise specified the term "halogen" or "halo" means fluorine, chlorine, bromine, or iodine.

As used herein, unless otherwise specified the term "haloalkyl" means -alkyl substituted with one or more halogens, wherein alkyl and halogen are defined as above, including —$CF_3$, —$CHF_2$, —$CH_2F$, —$CCl_3$, —$CHCl_2$, —$CBr_3$, —$CHBr_2$, —$CH_2CF_3$, —$CH_2CHF_2$, —$CH_2CH_2F$, and the like.

As used herein, unless otherwise specified the term "alkyl sulfonyl" means —$SO_2$-alkyl, wherein alkyl is defined as above, including —$SO_2$—$CH_3$, —$SO_2$—$CH_2CH_3$, —$SO_2$—$(CH_2)_2CH_3$, —$SO_2$—$(CH_2)_3CH_3$, —$SO_2$—$(CH_2)_4CH_3$, —$SO_2$—$(CH_2)_5CH_3$, and the like.

As used herein, unless otherwise specified the term "carboxyl" and "carboxy" mean —COOH or a salt thereof (e.g., —$COO^-Na^+$).

As used herein, unless otherwise specified the term "alkoxy" means —O-(alkyl), wherein alkyl is defined above, including —$OCH_3$, —$OCH_2CH_3$, —$O(CH_2)_2CH_3$, —$O(CH_2)_3CH_3$, —$O(CH_2)_4CH_3$, —$O(CH_2)_5CH_3$, and the like.

As used herein, unless otherwise specified the term "alkylthioether" means —S-(alkyl), wherein alkyl is defined above, including —$SCH_3$, —$SCH_2CH_3$, —$S(CH_2)_2CH_3$, —$S(CH_2)_3CH_3$, —$S(CH_2)_4CH_3$, —$S(CH_2)_5CH_3$, and the like.

As used herein, unless otherwise specified the term "haloalkoxy" means -alkoxy substituted with one or more halogens, wherein alkoxy and halogen are defined as above, including —$OCF_3$, —$OCHF_2$, —$OCH_2F$, —$OCCl_3$—$OCHCl_2$, —$OCBr_3$, —$OCHBr_2$, —$OCH_2CF_3$, —$OCH_2CHF_2$, —$OCH_2CH_2F$, and the like.

As used herein, unless otherwise specified the term "alkoxycarbonyl" means —C(=O)O-(alkyl), wherein alkyl is defined above, including —C(=O)O—$CH_3$, —C(=O)O—$CH_2CH_3$, —C(=O)O—$(CH_2)_2CH_3$, —C(=O)O—$(CH_2)_3CH_3$, —C(=O)O—$(CH_2)_4CH_3$, —C(=O)O—$(CH_2)_5CH_3$, and the like. In a preferred embodiment, the esters are biohydrolyzable (i.e., the ester is hydrolyzed to a carboxylic acid in vitro or in vivo).

As used herein, unless otherwise specified the term "acyl" means —CH(=O).

As used herein, unless otherwise specified the term "alkylcarbonyl" means —C(=O)-(alkyl), wherein alkyl is defined above, including —C(=O)—$CH_3$, —C(=O)—$CH_2CH_3$, —C(=O)—$(CH_2)_2CH_3$, —C(=O)—$(CH_2)_3CH_3$, —C(=O)—$(CH_2)_4CH_3$, —C(=O)—$(CH_2)_5CH_3$, and the like.

As used herein, unless otherwise specified the term "arylcarbonyl" means —C(=O)-(aryl), wherein aryl is defined below, including —C(=O)-phenyl, —C(=O)-tolyl, —C(=O)-anthracenyl, —C(=O)-fluorenyl, —C(=O)-indenyl, —C(=O)-azulenyl, —C(=O)phenanthrenyl —C(=O)-naphthyl, and the like.

As used herein, unless otherwise specified the term "carboxyalkyl" means -(alkyl)-carboxy, wherein alkyl and carboxy are defined above, including —$CH_2$—COOH, —$(CH_2)_2$—COOH, —$(CH_2)_3$—COOH, —$(CH_2)_4$—COOH, and the like.

As used herein, unless otherwise specified the term "alkoxyalkyl" means -(alkyl)-O-(alkyl), wherein each "alkyl" is independently an alkyl group as defined above, including —$CH_2OCH_3$, —$CH_2OCH_2CH_3$, —$(CH_2)_2OCH_2CH_3$, —$(CH_2)_2O(CH_2)_2CH_3$, and the like.

As used herein, unless otherwise specified the term "aryl" means a carbocyclic aromatic ring containing from 5 to 14 ring atoms. The ring atoms of a carbocyclic aryl group are all carbon atoms. Aryl ring structures include compounds having one or more ring structures such as mono-, bi-, or tricylcic compounds as well as benzo-fused carbocyclic moieties such as 5,6,7,8-tetrahydronaphthyl and the like. Preferably, the aryl group is a monocyclic ring or bicyclic ring. Representative aryl groups include phenyl, tolyl, anthracenyl, fluorenyl, indenyl, azulenyl, phenanthrenyl and naphthyl. A carbocyclic aryl group can be unsubstituted or substituted.

As used herein, unless otherwise specified the term "heteroaryl" means a carbocyclic aromatic ring containing from 5 to 14 ring atoms and the ring atoms contain at least one heteroatom, preferably 1 to 3 heteroatoms, independently selected from nitrogen, oxygen, or sulfur. Heteroaryl ring structures include compounds having one or more ring structures such as mono-, bi-, or tricyclic compounds as well as fused heterocyclic moieties. Representative heteroaryls are triazolyl, tetrazolyl, oxadiazolyl, pyridyl, furyl, benzofuranyl, thiophenyl, thiazolyl, benzothiophenyl, benzoisoxazolyl, benzoisothiazolyl quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl cinnolinyl phthalazinyl, quinazolinyl, benzoquinazolinyl, acridinyl, pyrimidyl, oxazolyl benzo[1,3]dioxole and 2,3 dihydrobenzo[1,4]dioxine. A group can be unsubstituted or substituted.

As used herein, unless otherwise specified the term "aryloxy" means —O-aryl group, herein aryl is as defined above, including, but not limited to —O-phenyl, —O-tolyl, —O-anthracenyl, —O-fluorenyl, —O-indenyl, —O-azulenyl, —O-phenanthrenyl and —O-naphthyl. An aryloxy group can be unsubstituted or substituted.

As used herein, unless otherwise specified the term "arylalkyl" means -(alkyl)-(aryl), wherein alkyl and aryl are defined above, including, but not limited to —(CH$_2$)phenyl, —(CH$_2$)$_2$phenyl, —(CH$_2$)$_3$phenyl, —CH(Phenyl)$_2$, —CH(phenyl)$_3$, —(CH$_2$)tolyl, —(CH$_2$)anthracenyl, —(CH$_2$)fluorenyl, —(CH$_2$)indenyl, —(CH$_2$)azulenyl, —(CH$_2$)naphthyl, and the like.

As used herein, unless otherwise specificed the term "alkylaryl" means -(aryl)-(alkyl), wherein aryl and aryl are defined above, including, but not limited to -phenyl-(CH$_3$)$_5$, phenyl-(CH$_3$)$_4$, phenyl-(CH$_3$)$_3$, phenyl-(CH$_3$)$_2$, phenyl-(CH$_3$), -phenyl-(CH$_2$CH$_3$)$_5$, phenyl-(CH$_2$CH$_3$)$_4$, phenyl-(CH$_2$CH$_3$)$_3$, phenyl-(CH$_2$CH$_3$)$_2$, phenyl-(CH$_2$CH$_3$), and the like wherein each alkyl group can be further substituted.

As used herein, unless otherwise specified the term "heteroarylalkyl" means -(alkyl)-(heteroaryl), wherein alkyl and heteroaryl are defined above, including, but not limited to, —(CH$_2$)Pyridyl, —CH$_2$)$_2$ pyridyl, —(CH$_2$)$_3$ pyridyl, —CH(Pyridyl)$_2$, —C(pyridyl)$_3$, —(CH$_2$)triazolyl, —(CH$_2$)thiazolyl, —(CH$_2$)tetrazolyl, —(CH$_2$)oxadiazolyl, —(CH$_2$)furyl, —(CH$_2$)benzofuranyl, —(CH$_2$)thiophenyl, —(CH$_2$)benzothiophenyl, and the like.

As used herein, unless otherwise specified the term "alkylheteroaryl" means -(heteroaryl)-(alkyl), wherein heteroaryl and alkyl are defined above, including, but not limited to, -pyridyl-(CH$_3$), -triazolyl-(CH$_3$), -thiazolyl-(CH$_3$), -tetrazolyl-(CH$_3$), -oxadiazolyl-(CH$_3$), -furyl-(CH$_3$), -benzofuranyl-(CH$_3$), -thiophenyl-(CH$_3$), -benzothiophenyl-(CH$_3$), and the like wherein each alkyl group can be further substituted.

As used herein, unless otherwise specified the term "arylalkyloxy" means —O-(alkyl)-(aryl), wherein alkyl and aryl are defined above, including, but not limited to —O—(CH$_2$)$_2$phenyl, —O—(CH$_2$)$_3$phenyl, —O—CH(phenyl)$_2$, —O—CH(phenyl)$_3$, —O—(CH$_2$)tolyl, —O—(CH$_2$)anthracenyl, —O—CH$_2$)fluorenyl, —O—(CH$_2$)indenyl, —O(CH$_2$)azulenyl, —O—(CH$_2$)naphthyl, and the like.

As used herein, unless otherwise specified the term "cycloalkyl" means a monocyclic or polycyclic saturated ring comprising carbon and hydrogen atoms and having no carbon-carbon multiple bonds. A cycloalkyl group can be unsubstituted or substituted. Examples of cycloalkyl groups include, but are not limited to, (C$_3$-C$_7$)cycloalkyl groups, including cyclopropyl, cyclobutyl, cyclopentyl, cyclohexyl, and cycloheptyl, and saturated cyclic and bicyclic terpenes. A cycloalkyl group can be unsubstituted or substituted. Preferably, the cycloalkyl group is a monocyclic ring or bicyclic ring.

As used herein, unless otherwise specified the terms "heterocyclyl" and "heterocyclo" mean a monocyclic or polycyclic ring comprising carbon and hydrogen atoms, optionally having 1 or 2 multiple bonds, and the ring atoms contain at least one heteroatom, preferably 1 to 3 heteroatoms, independently selected from nitrogen, oxygen, and sulfur. Heterocyclyl ring structures include, but are not limited to compounds having one or more ring structures such as mono-, bi-, or trycylic compounds. Preferably, the heterocyclyl group is a monocyclic ring or bicyclic ring. Representative heterocycles include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl or tetrahydrothiopyranyl and the like. A heterocyclyl ring can be unsubstituted or substituted.

As used herein, unless otherwise specified the term "cycloalkyloxy" means —O-(cycloalkyl), wherein cycloalkyl is defined above, including —O-cyclopropyl, —O-cyclobutyl, —O-cyclopentyl, —O-cyclohexyl, —O-cycloheptyl and the like.

As used herein, unless otherwise specified the term "cycloalkylalkyl" means -(alkyl)-(cycloalkyl), wherein cycloalkyl and alkyl are defined above, including, but not limited to —CH$_2$-cyclopropyl, —CH$_2$-cyclobutyl, —CH$_2$-cyclopentyl, —(CH$_2$)$_2$-cyclohexyl, —(CH$_2$)$_3$-cyclohexyl, —(CH$_2$)$_4$-cyclohexyl, —CH$_2$-cycloheptyl and the like.

As used herein, unless otherwise specified the term "heterocycloalkyl" means -(alkyl)(heterocyclo), wherein heterocyclo and alkyl are defined above, including, but not limited to —CH$_2$-morpholinyl, —CH$_2$-pyrrolidinonyl, —CH$_2$-pyrrolidinyl, —(CH$_2$)$_2$-piperidinyl, —(CH$_2$)$_3$-piperidinyl, —(CH$_2$)$_4$-piperidinyl, —CH$_2$-hydantoinyl and the like.

As used herein, unless otherwise specified the term "cycloalkylalkyloxy" means —O-(alkyl)-(cycloalkyl), wherein cycloalkyl and alkyl are defined above, including, but not limited to —O—CH$_2$-cyclopropyl, —O—CH$_2$-cyclobutyl, —O—CH$_2$-cyclopentyl, —O—(CH$_2$)$_2$-cyclohexyl, —O—(CH$_2$)$_3$-cyclohexyl, —O—(CH$_2$)$_4$-cyclohexyl, —O—CH$_2$-cycloheptyl and the like.

As used herein, unless otherwise specified the term "heterocycloalkyloxy" means —O-(alkyl)-(heterocyclo), wherein heterocyclo and alkyl are defined above, including, but not limited to —O—CH$_2$-morpholinyl, —O—CH$_2$-pyrrolidinonyl, —O—CH$_2$-pyrrolidinyl, —O—(CH$_2$)$_2$-piperidinyl, —O—(CH$_2$)$_3$-piperidinyl, —O—(CH$_2$)$_4$-piperidinyl, —O—CH$_2$-hydantoinyl and the like.

As used herein, unless otherwise specified the term "aminoalkoxy" means —O-(alkyl)-NH$_2$, wherein alkyl is defined above, including, but not limited to —O—CH$_2$—NH$_2$, —O—(CH$_2$)$_2$—NH$_2$, —O—(CH$_2$)$_3$—NH$_2$, —O—CH$_2$)$_4$—NH$_2$, —O—(CH$_2$)$_5$—NH$_2$, and the like.

As used herein, unless otherwise specified the term "alkylamino" means —NH(alkyl) or —N(alkyl)(alkyl), wherein alkyl is defined above, including, but not limited to NHCH$_3$, —NHCH$_2$CH$_3$, —NH(CH$_2$)$_2$CH$_3$, —NH(CH$_2$)$_3$CH$_3$, —NH(CH$_2$)$_4$CH$_3$, —NH(CH$_2$)$_5$CH$_3$, —N(CH$_3$)$_2$, N(CH$_2$CH$_3$)$_2$, —N((CH$_2$)$_2$CH$_3$)$_2$, —N(CH$_3$)(CH$_2$CH$_3$), and the like.

As used herein, unless otherwise specified the term "arylamino" means —NH(aryl), wherein aryl is defined above, including, but not limited to —NH(phenyl), —NH(tolyl), —NH(anthracenyl), —NH(fluorenyl), —NH(indenyl), —NH(azulenyl), —NH(pyridinyl), —NH(naphthyl), and the like.

As used herein, unless otherwise specified the term "arylalkylamino" means —NH-(alkyl)-aryl), wherein alkyl and aryl are defined above, including, but not limited to —NH—CH$_2$-(Phenyl), —NH—CH$_2$— (tolyl), —NH—CH$_2$-(anthracenyl), —NH—CH$_2$— (fluorenyl), —NH—CH$_2$-(indenyl), —NH—CH$_2$-(azulenyl), —NH—CH$_2$-pyridinyl), —NH—CH$_2$-(naphthyl), —NH—(CH$_2$)$_2$-(phenyl) and the like.

As used herein, unless otherwise specified the term "cycloalkylamino" means —NH-(cycloalkyl), wherein cycloalkyl is defined above, including, but not limited to —NH-cyclopropyl, —NH-cyclobutyl, —NH-cyclopentyl, —NH-cyclohexyl, —NH-cycloheptyl, and the like.

As used herein, unless otherwise specified the term "aminoalkyl" means -(alkyl)-NH$_2$, wherein alkyl is defined above, including, but not limited to —CH$_2$—NH$_2$, —(CH$_2$)$_2$—NH$_2$, —(CH$_2$)$_3$—NH$_2$, —(CH$_2$)$_4$—NH$_2$, —(CH$_2$)$_5$—NH$_2$ and the like.

As used herein, unless otherwise specified the term "alkylaminoalkyl" means -(alkyl)-NH(alkyl) or -(alkyl)N(alkyl)(alkyl), wherein each "alkyl" is independently an alkyl group defined above, including, but not limited to —CH$_2$—NH—CH$_3$, —CH$_2$—NHCH$_2$CH$_3$, —CH$_2$—NH(CH$_2$)$_2$CH$_3$, —CH$_2$—NH(CH$_2$)$_3$CH$_3$, —CH$_2$—NH(CH$_2$)$_4$CH$_3$, —CH$_2$—NH(CH$_2$)$_5$CH$_3$, —(CH$_2$)$_2$—NH—CH$_3$, —CH$_2$—N(CH$_3$)$_2$, —CH$_2$—N(CH$_2$CH$_3$)$_2$, —CH$_2$—N((CH$_2$)$_2$CH$_3$)$_2$, —CH$_2$—N(CH$_3$)(CH$_2$CH$_3$), —(CH$_2$)$_2$—N(CH$_3$)$_2$, and the like.

As used herein, the term "liquid chromatography-mass spectrometry (LC/MS)" means an analytical method in which a sample is fractionated using liquid chromatography, and the column eluant is characterized by mass spectrometry.

As used herein, a "therapeutically effective amount" refers to that amount of the compound of the invention or other active ingredient sufficient to provide a therapeutic benefit in the treatment or management of the disease or to delay or minimize symptoms associated with the disease. Further, a therapeutically effective amount with respect to a compound of the invention means that amount of therapeutic agent alone, or in combination with other therapies, that provides a therapeutic benefit in the treatment or management of the disease. Used in connection with an amount of a compound of the invention, the term can encompass an amount that improves overall therapy, reduces or avoids symptoms or causes of disease, or enhances the therapeutic efficacy of or synergies with another therapeutic agent.

As used herein, a "prophylactically effective amount" refers to that amount of a compound of the invention or other active ingredient sufficient to result in the prevention, recurrence or spread of the disease. A prophylactically effective amount may refer to the amount sufficient to prevent initial disease, the recurrence or spread of the disease or the occurrence of the disease in a patient, including but not limited to those predisposed to the disease. A prophylactically effective amount may also refer to the amount that provides a prophylactic benefit in the prevention of the disease. Further, a prophylactically effective amount with respect to a compound of the invention means that amount alone, or in combination with other agents, that provides a prophylactic benefit in the prevention of the disease. Used in connection with an amount of a compound of the invention, the term can encompass an amount that improves overall prophylaxis or enhances the prophylactic efficacy of or synergies with another prophylactic agent.

As used herein, a "therapeutic protocol" refers to a regimen of timing and dosing of one or more therapeutic agents.

As used herein, a "prophylactic protocol" refers to a regimen of timing and dosing of one or more prophylactic agents.

A used herein, a "protocol" includes dosing schedules and dosing regimens.

As used herein, "in combination" refers to the use of more than one prophylactic and/or therapeutic agents.

As used herein, the terms "manage", "managing" and "management" refer to the beneficial effects that a subject derives from a prophylactic or therapeutic agent, which does not result in a cure of the disease. In certain embodiments, a subject is administered one or more prophylactic or therapeutic agents to "manage" a disease so as to prevent the progression or worsening of the disease.

As used herein, the terms "prevent", "preventing" and "prevention" refer to the prevention of the onset, recurrence or spread of the disease in a subject resulting from the administration of a prophylactic or therapeutic agent As used herein, the terms "treat", "teating" and "teatment" refer to the eradication or amelioration of the disease or symptoms associated with the disease. In certain embodiments, such terms refer to minimizing the spread or worsening of the disease resulting from the administration of one or more prophylactic or therapeutic agents to a subject with such a disease.

As used herein, the term "pharmaceutically acceptable salts" refer to salts prepared from pharmaceutically acceptable non-toxic acids or bases including inorganic acids and bases and organic acids and bases. Suitable pharmaceutically acceptable base addition salts for the compound of the present invention include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences*, 18th eds., Mack Publishing, Easton Pa. (1990) or *Remington: The Science and Practice of Pharmacy*, 19th eds., Mack Publishing, Easton Pa. (1995).

As used herein and unless otherwise indicated, the term "polymorph" refers to solid crystalline forms of a compound of the present invention or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g. differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g. tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "hydrate" means a compound of the present invention or a salt thereof, that further includes a stoichiometric or non-stoichiometric amount of water bound by non-covalent intermolecular forces.

As used herein, he term "clathrate" means a compound of the present invention or a salt thereof in the form of a crystal lattice that contains spaces (e.g. channels) that have a guest molecule (e.g., a solvent or water) trapped within.

As used herein and unless otherwise indicated, the term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable groups such as biohydrolyzable amides, biohydrolyzable esters, biohydrolyzable carbamates, biohydrolyzable carbonates, biohydrolyzable ureides, and biohydrolyzable phosphate analogues (e.g., monophosphate, diphosphate or triphosphate). Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6th ed. (Donald J. Abraham ed., 2001, Wiley) and *Design and Application of Prodrugs* (H. Bundgaard ed., 1985, Harwood Academic Publishers Gmfh).

As used herein and unless otherwise indicated, the terms "biohydrolyzable amide," "biohydrolyzable ester," "biohydrolyzable carbamate," "biohydrolyzable carbonate," "biohydrolyzable ureido," "biohydrolyzable phosphate" (collectively referred to herein as a "biohydrolyzable group(s)") mean an amide, ester, carbamate, carbonate, ureido, or phosphate, respectively, of a compound that either 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters. Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein and unless otherwise indicated, the term "optically pure" or "stereomerically pure" means one stereoisomer of a compound is substantially free of other stereoisomers of that compound. For example, a stereomerically pure compound having one chiral center will be substantially free of the opposite enantiomer of the compound. A stereomerically pure a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "enantiomerically pure" means a stereomerically pure composition of a compound having one chiral center.

It should be noted that if there is a discrepancy between a depicted structure and a name given that structure, the depicted structure controls. In addition, if the stereochemistry of a structure or a portion of a structure is not indicated with, for example, bold or dashed lines, the structure or portion of the structure is to be interpreted as encompassing all stereoisomers of it.

4. DETAILED DESCRIPTION OF THE INVENTION

4.1 Compounds of the Invention

As stated above, the present invention encompasses compounds of formula I, compositions comprising compounds of formula I, and methods of use thereof. Compounds of formula I have the structure:

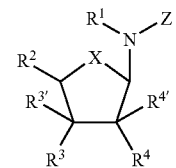

I or a pharmaceutically acceptable salt, hydrate, solvate, clathrate, racemate or stereoisomer thereof, wherein:

Z is substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, substituted or unsubstituted arylcarbonyl;

X is $CH_2$, O, S or NH;

$R^1$ is hydrogen, substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl;

$R^2$ is substituted or unsubstituted alkyl, carboxy, amido, acyl, alkylcarbonyl, halogen, a biohydrolyzable group, $OP(O)_3{}^{2-}$; $O[P(O)_3]_2{}^{3-}$; $O[P(O)_3]_3{}^{4-}$, $N_3$, $CH_2-NR_6R_7$ or $CH_2-OR^6$;

$R^3$, $R^{3'}$, $R^4$ and $R^{4'}$ are at each occurence independently $OR^7$, $OR^8$, hydrogen, halogen, substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, substituted or unsubstituted arylcarbonyl, substituted or unsubstituted alkylcarbonyl, a biohydrolyzable group, or $R^3$ and $R^4$ taken together form a bond, or $R^3$ and $R^4$ taken together with the atoms to which they are attached form a substituted or unsubstituted heterocyclo, or $R^3$ and $R^{3'}$ and/or $R^4$ and $R^{4'}$ taken together with the carbon to which they are attached form C(=O); and $R^6$, $R^7$ and $R^8$ are at each occurrence independently hydrogen, substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, substituted or unsubstituted arylcarbonyl, substituted or unsubstituted alkylcarbonyl, a biohydrolyzable group, or $R^3$ and $R^4$ taken together with the atoms to which they are attached form a substituted or unsubstituted heterocyclo.

In one embodiment, Z is monocyclic. In another embodiment, Z is bicyclic. In another embodiment, Z is tricyclic. In another embodiment, Z is a 6-membered monocyclic ring.

In a preferred embodiment, Z is substituted or unsubstituted pyridinyl.

In another preferred embodiment, Z is substituted or unsubstituted pyrimidinyl.

In another preferred embodiment, Z is substituted or unsubstituted pyrazinyl.

In another preferred embodiment, Z is substituted or unsubstituted quinolinyl.

In another preferred embodiment, X is O.

In another preferred embodiment, $R^2$ is $CH_2$—$OR^6$.

In another preferred embodiment, $R^6$ is H.

It should be recognized that the invention includes embodiments which exclude clitocine and instead include other compounds of the invention. In other words, in one embodiment, the compound of formula I is not clitocine (i.e., 6-amino-5-nitro-4-(β-D-ribofuranosylamino)pyrimidine).

In another embodiment, compounds of formula I have the structure:

II or a pharmaceutically acceptable salt, hydrate, solvate, clathrate, racemate or stereoisomer thereof wherein:

X is $CH_2$, O, S or NH;

$R^1$ is hydrogen, substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl;

$R^2$ is substituted or unsubstituted alkyl, carboxy, amido, acyl, alkylcarbonyl, halogen, a biohydrolyzable group, $OP(O)_3^{2-}$, $O[P(O)_3]_2^{3-}$, $O[P(O)_3]_3^{4-}$, $N_3$, $CH_2$—$NR_6R_7$ or $CH_2$—$OR^6$;

$R^3$, $R^{3'}$, $R^4$ and $R^{4'}$ are at each occurence independently $OR^7$, $OR^8$, hydrogen, halogen, substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, substituted or unsubstituted arylcarbonyl, substituted or unsubstituted alkylcarbonyl, a biohydrolyzable group, or $R^3$ and $R^4$ taken together from a bond, or $R^3$ and $R^4$ taken together with the atoms to which they are attached form a substituted or unsubstituted heterocyclo, or $R^3$ and $R^{3'}$ and/or $R^4$ and $R^{4'}$ taken together with the carbon to which they are attached form C(=O);

$R^6$, $R^7$ and $R^8$ are at each occurrence independently hydrogen, substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, substituted or unsubstituted arylcarbonyl, substituted or unsubstituted alkylcarbonyl, a biohydrolyzable group, or $R^7$ and $R^8$ taken together with the atoms to which they are attached form a substituted or unsubstituted heterocyclo;

A and B are each independently C or N;

$Y^1$-$Y^5$ are each independently hydrogen, hydroxy, halogen, nitro, cyano, sulfate, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, alkoxy, alkylthioether, carboxyalkyl, carbonylalkyl, amino, $N^5R^{5'}$, amido, or alkoxycarbonyl, wherein if B is N, $Y^3$ can also be $O^-$ and if A is N, $Y^5$ can also be $O^-$, and wherein $Y^3$ is not present if B is N and $Y^5$ is not present if A is N; and $R^5$ and $R^{5'}$ are each independently hydrogen, substituted or unsubstituted alkyl, substituted or unsubstituted alkenyl, substituted or unsubstituted alynyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl substituted or unsubstituted heterocycloalkyl.

In a preferred embodiment, $Y^1$ is halogen, nitro, sulfate, alkoxycarbonyl, cyano or carbonylalkyl.

In another preferred embodiment, $Y^2$ is halogen, nitro, sulfate, alkoxycarbonyl, cyano or carbonylalkyl.

In another preferred embodiment, $R^2$ is $CH_2$—$OR^6$.

In another preferred embodiment, $R^6$ is H.

In another preferred embodiment, $R^1$ is H.

It should be recognized that the invention includes embodiments which exclude clitocine and instead include other compounds of the invention. In other words, in one embodiment, the compound of formula II is not clitocine (i.e., 6-amino-5-nitro-4-(β-D-ribofuranosylamino)pyrimidine).

In another embodiment, compounds of formula I have the structure:

III wherein A, B, $R^1$, $R^2$, $R^3$, $R^{3'}$, $R^4$, $R^{4'}$, $Y^1$ and $Y^2$ are as described for formula I.

In a preferred embodiment, $R^2$ is $CH_2$—$OR^6$.
In another preferred embodiment, $R^6$ is H.
In another embodiment, compounds of formula I have the structure:

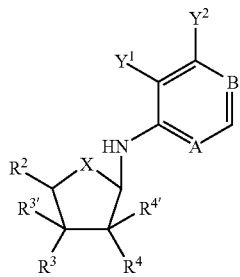

IV wherein A, B, X, $R^2$, $R^3$, $R^{3'}$, $R^4$, $R^{4'}$, $Y^1$ and $Y^2$ are as described for formula I.

In a preferred embodiment, $R^2$ is $CH_2$—$OR^6$.
In another preferred embodiment, $R^6$ is H.
In another embodiment, compounds of formula I have the structure:

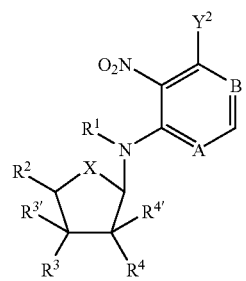

V wherein A, B, X, $R^1$, $R^2$, $R^3$, $R^{3'}$, $R^4$, $R^{4'}$ and $Y^2$ are as described for formula I.

In a preferred embodiment, $R^2$ is $CH_2$—$OR^6$.
In another preferred embodiment, $R^6$ is H.
In another embodiment, compounds of formula I have the structure:

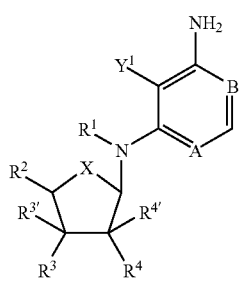

VI wherein A, B, X, $R^1$, $R^2$, $R^3$, $R^{3'}$, $R^4$, $R^{4'}$ nd $Y^1$ are as described for formula I.

In a preferred embodiment, $R^2$ is $CH_2$—$OR^6$.
In another preferred embodiment, $R^6$ is H.
In another embodiment, compounds of formula I have the structure:

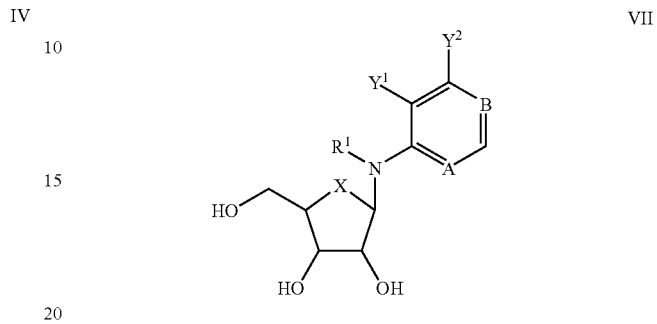

VII wherein A, B, X, $R^1$, $Y^1$ and $Y^2$ are as described for formula I.

In another embodiment, compounds of formula I have the structure:

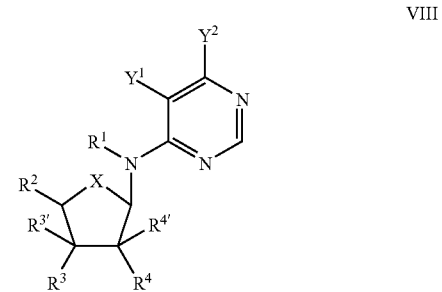

VIII wherein X, $R^1$, $R^2$, $R^3$, $R^{3'}$, $R^4$, $R^{4'}$, $Y^1$ and $Y^2$ are as described for formula I.

In a preferred embodiment, $R^2$ is $CH_2$—$OR^6$.
In another preferred embodiment, $R^6$ is H.
In another embodiment, the compound of formula I has the structure:

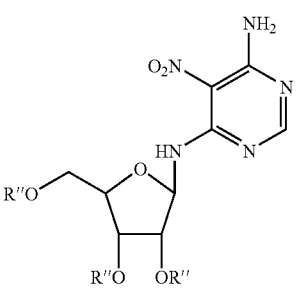

IX

Wherein each occurrence of R'' is independently hydrogen, $OP(O_3)^{-2}$, $C(=O)CH_3$ or a biohydrolyzable group.

Exemplary compounds of the present invention include those listed below in Table 1 (data has been presented where it is available):

TABLE 1

| Compound | | Compound Name | Melting Point (° C.) or [M + H]+ | Activity |
|---|---|---|---|---|
| 1 | | 6-amino-5-nitro-4-(β-D-ribofuranosylamino)-pyrimidine | 180° C. (dec.) | *** |
| 2 | | 6-(N-methylamino)-5-nitro-4-(β-D-ribo-furanosylamino)pyrimidine | 130-135° C. | ** |
| 3 | | 5,6-Diamino-4-(β-D-ribofuranosyl-amino)pyrimidine | [M + H]+ = 258 | * |
| 4 | | 3-Nitro-2-(β-D-ribofuranosyl-amino)pyridine | [M + H]+ = 271 | *** |
| 5 | | 5-Nitro-2-(β-D-ribofuranosyl-amino)pyridine | [M + H]+ = 272 | * |

TABLE 1-continued

| Compound | | Compound Name | Melting Point (° C.) or [M + H]⁺ | Activity |
|---|---|---|---|---|
| 6 | | (1R,2S,3R,5R)-3-(6-Amino-5-nitro-pyrimidin-4-ylamino)-5-hydroxymethyl-cyclopentane-1,2-diol | [M + H]⁺ = 286 | 0 |
| 7 | | (1S,2R,3S,5S)-3-(6-Amino-5-nitro-pyrimidin-4-ylamino)-5-hydroxymethyl-cyclopentane-1,2-diol | [M + H]⁺ = 286 | 0 |
| 8 | | 6-methoxy-3-nitro-2-(β-D-ribofuranosyl-amino)pyridine | 90° C. (dec.) | 0 |
| 9 | | 6-(dimethylamino)-5-nitro-4-(β-D-ribo-furanosylamino) pyrimidine | [M + H]⁺ = 316 | 0 |
| 10 | | 6-(thiomethyl)-5-nitro-4-(β-D-ribo-furanosylamino) pyrimidine | 155-158° C. | * |

TABLE 1-continued

| Compound | | Compound Name | Melting Point (° C.) or [M + H]+ | Activity |
|---|---|---|---|---|
| 11 | | 5-nitro-4-methyl-2-(β-D-ribofuranosyl-amino)pyridine | [M + H]+ = 286 | * |
| 12 | | 6-amino-5-nitro-4-(2,3-O-isopropylidene-β-D-ribofuranosylamino)pyrimidine | 145-147° C. | 0 |
| 13 | | 6-(2-hydroxy-ethylamino)-5-nitro-4-(β-D-ribo-furanosylamino)pyrimidine | [M + H]+ = 332 | 0 |
| 14 | | 6-(ethylamino)-5-nitro-4-(β-D-ribo-furanosylamino)pyrimidine | 175° C. (dec) | 0 |
| 15 | | 6-(4-methoxy-benzylamino)-5-cyano-4-(β-D-ribo-furanosylamino)pyrimidine | [M + H]+ = 388 | 0 |

TABLE 1-continued

| | Compound | Compound Name | Melting Point (° C.) or [M + H]+ | Activity |
|---|---|---|---|---|
| 16 | | 3-cyano-2-(β-D-ribofuranosyl-amino)pyridine | [M + H]+ = 252 | * |
| 17 | | 6-hydroxy-5-nitro-4-(β-D-ribofuranosylamino)pyrimidine | 197° C. (dec.) | * |
| 18 | | 6-amino-5-nitro-4-(β-D-xylofuranosylamino)-pyrimidine | 227-228° C. | 0 |
| 19 | | 6-amino-5-nitro-4-(β-L-ribofuranosylamino)-pyrimidine | 226-227° C. | ** |
| 20 | | 6-amino-5-nitro-4-(5-deoxy-5-fluoro-β-D-ribofuranosylamino)-pyrimidine | 129-130° C. | * |

TABLE 1-continued

| Compound | Compound Name | Melting Point (° C.) or [M + H]+ | Activity |
|---|---|---|---|
| 21 | 6-amino-5-nitro-4-(5-deoxy-5-azido-β-D-ribofuranosylamino)-pyrimidine | 204-205° C. | * |
| 22 | 6-amino-5-nitro-4-(α-D-ribofuranosylamino)-pyrimidine | 187-214° C. | *** |
| 23 | 6-Amino-5-nitro-4-[(5-O-acetyl-β-D-ribofuranosyl)amino]pyrimidine | 102-125° C. | *** |
| 24 | 6-Amino-5-nitro-4-[(2,3,5-tri-O-benzoyl-β-D-ribofuranosyl)amino]pyrimidine | [M + H]+ = 600 | ** |
| 25 | Methyl 6-amino-4-(β-D-ribofuranosylamino)pyrimidine-5-carboxylate | 154-155° C. | * |

TABLE 1-continued

| Compound | | Compound Name | Melting Point (° C.) or [M + H]+ | Activity |
|---|---|---|---|---|
| 26 | | Methyl 6-chloro-4-(β-D-ribofuranosylamino)pyrimidine-5-carboxylate | 161-162° C. | 0 |
| 27 | | Methyl 6-amino-4-(α-D-ribofuranosylamino)pyrimidine-5-carboxylate | 129-130° C. | * |
| 28 | | Methyl 6-chloro-4-(α-D-ribofuranosylamino)pyrimidine-5-carboxylate | 135° C. (dec.) | 0 |
| 30 | | 5-(6-Amino-5-nitro-pyrimidin-4-ylamino)-3,4-dihydroxy-tetrahydro-furan-2-carboxylic acid | | |
| 31 | | 5-(6-Amino-5-nitro-pyrimidin-4-ylamino)-3,4-dihydroxy-tetrahydro-furan-2-carboxylic acid amide | | |

TABLE 1-continued

| | Compound | Compound Name | Melting Point (° C.) or [M + H]⁺ | Activity |
|---|---|---|---|---|
| 32 | | 5-(6-Amino-5-nitro-pyrimidin-4-ylamino)-3,4-dihydroxy-tetrahydro-furan-2-carbaldehyde | | |
| 33 | | 2-(6-Amino-5-nitro-pyrimidin-4-ylamino)-5-(1-hydroxy-ethyl)-tetrahydro-furan-3,4-diol | | |
| 34 | | 2-(6-Amino-5-nitro-pyrimidin-4-ylamino)-5-methyl-tetrahydro-furan-3,4-diol | | |
| 35 | | 2-(4-Amino-3-nitro-pyridin-2-ylamino)-5-hydroxymethyl-tetrahydro-furan-3,4-diol | | |
| 36 | | 2-(5-Amino-4-nitro-pyridin-3-ylamino)-5-hydroxymethyl-tetrahydro-furan-3,4-diol | | |

TABLE 1-continued

| | Compound | Compound Name | Melting Point (° C.) or [M + H]+ | Activity |
|---|---|---|---|---|
| 37 | | 5-(6-Amino-5-nitro-pyrimidin-4-ylamino)-2-hydroxymethyl-tetrahydro-furan-3-ol | | |
| 38 | | 5-(6-Amino-5-nitro-pyrimidin-4-ylamino)-4-fluoro-2-hydroxymethyl-tetrahydro-furan-3-ol | | |
| 39 | | 5-(6-Amino-5-nitro-pyrimidin-4-ylamino)-4-fluoro-2-hydroxymethyl-tetrahydro-furan-3-ol | | |
| 40 | | 5-(6-Amino-5-nitro-pyrimidin-4-ylamino)-4,4-difluoro-2-hydroxymethyl-tetrahydro-furan-3-ol | | |
| 41 | | 2-(6-Amino-5-nitro-pyrimidin-4-ylamino)-4-fluoro-5-hydroxymethyl-tetrahydro-furan-3-ol | | |

TABLE 1-continued

| Compound | | Compound Name | Melting Point (° C.) or [M + H]+ | Activity |
|---|---|---|---|---|
| 42 | | 2-(6-Amino-5-nitro-pyrimidin-4-ylamino)-4-fluoro-5-hydroxymethyl-tetrahydro-furan-3-ol | | |
| 43 | | 2-(6-Amino-5-nitro-pyrimidin-4-ylamino)-4,4-difluoro-5-hydroxymethyl-tetrahydro-furan-3-ol | | |
| 44 | | [5-(6-Amino-5-nitro-pyrimidin-4-ylamino)-2,5-dihydro-furan-2-yl]-methanol | | |
| 45 | | 5-(6-Amino-5-nitro-pyrimidin-4-ylamino)-2-hydroxymethyl-3-methyl-tetrahydro-furan-3,4-diol | | |
| 46 | | 2-(6-Amino-5-nitro-pyrimidin-4-ylamino)-4-hydroxy-5-hydroxymethyl-dihydro-furan-3-one | | |

TABLE 1-continued

| Compound | | Compound Name | Melting Point (° C.) or [M + H]+ | Activity |
|---|---|---|---|---|
| 47 | | 5-(6-Amino-5-nitro-pyrimidin-4-ylamino)-4-hydroxy-2-hydroxymethyl-dihydro-furan-3-one | | |
| 48 | | 2-Aminomethyl-5-(6-amino-5-nitro-pyrimidin-4-ylamino)-tetrahydro-furan-3,4-diol | | |
| 49 | | 2-(6-Amino-5-nitro-pyrimidin-4-ylamino)-5-(2-hydroxy-ethyl)-tetrahydro-furan-3,4-diol | | |
| 50 | | 2-(6-Amino-5-nitro-pyrimidin-4-ylamino)-5-hydroxymethyl-tetrahydro-thiophene-3,4-diol | | |
| 51 | | 2-(2-Amino-3-nitro-pyridin-4-ylamino)-5-hydroxymethyl-tetrahydro-furan-3,4-diol | | |

TABLE 1-continued

| | Compound | Compound Name | Melting Point (° C.) or [M + H]+ | Activity |
|---|---|---|---|---|
| 52 | | 4-amino-6-(3,4-dihydroxy-5-hydroxymethyl-tetrahydro-furan-2-ylamino)-pyrimidine-5-carboxylate | | |
| 53 | | 4-Amino-6-(3,4-dihydroxy-5-hydroxymethyl-tetrahydro-furan-2-ylamino)-pyrimidine-5-carboxylic acid | | |
| 54 | | 2-Hydroxymethyl-5-(5-nitro-pyrimidin-4-ylamino)-tetrahydro-furan-3,4-diol | | |
| 55 | | 2-(6-Amino-5-nitro-pyridazin-4-ylamino)-5-hydroxymethyl-tetrahydro-furan-3,4-diol | | |
| 56 | | 2-(5-Amino-4-nitro-pyridazin-3-ylamino)-5-hydroxymethyl-tetrahydro-furan-3,4-diol | | |

TABLE 1-continued

| Compound | Compound Name | Melting Point (° C.) or [M + H]+ | Activity |
|---|---|---|---|
| 57 | | | |
| 58 | | | |
| 59 | | | |

Melting points (where available) were obtained on an Electrothermal MeltTemp™ apparatus and are uncorrected. Mass spec data (where available) was obtained on a Micro Mass (Beverly, Mass.) ESI-MS (electrospray ionization-mass spectrometer).

Activity measurements in Table 1 were performed in a cell-based luciferase reporter assay (as described in Section 4.2) comprising a luciferase reporter construct containing a UGA premature termination codon that was stably transfected in 293T Human Embryonic Kidney cells. Gentamicin, a small molecule known to allow readthrough of premature termination codons, was used as an internal standard. Activity measurements are based on the qualitative ratio between the minimum concentration of compound required to produce a given protein in a cell versus the amount of protein produced by the cell at that concentration. Compounds which were found to have either or both very high potency and very high efficacy of protein synthesis are classified as "*". Compounds which were found to have significant potency and/or efficacy of protein synthesis were classified as "". Similarly, compounds which were found to have potency and/or efficacy of protein synthesis were classified as "*".

The present invention encompasses the in vitro or in vivo use of a compound of the invention, and the incorporation of a compound of the invention into pharmaceutical compositions and single unit dosage forms useful in the treatment and prevention of a variety of diseases and disorders. Specific diseases and disorders include those ameliorated by the suppression of a nonsense mutation in messenger RNA.

Pharmaceutical compositions including dosage forms of the invention, which comprise a compound of the invention, can be used in the methods of the invention.

Without being limited by theory, it is believed that a compound of the invention can modulate premature translation termination and/or nonsense-mediated mRNA decay. Consequently, a first embodiment of the invention relates to a method of modulating premature translation termination and/or nonsense-mediated mRNA decay comprising contacting a cell exhibiting a nonsense mutation with an effective amount of a compound of the invention. In a particular embodiment, the invention relates to a method of inducing nonsense suppression comprising contacting a cell exhibiting a nonsense mutation with an effective amount of a compound of the invention.

4.2 Biological Assays and Animal Studies

The test compounds identified in the nonsense suppression assay (for convenience referred to herein as a compound of the invention) can be tested for biological activity using host cells containing or engineered to contain the target RNA element coupled to a functional readout system. For example, the lead compound can be tested in a host cell engineered to contain the RNA with the premature translation termination codon controlling the expression of a reporter gene. In this example, the lead compounds are assayed in the presence or absence of the RNA with the premature translation termination codon. Compounds that modulate premature translation termination and/or nonsense-mediated mRNA decay in vivo will result in increased expression of the full-length gene, i.e., past the premature termination codon. Alternatively, a phenotypic or physiological readout can be used to assess activity of the target RNA with the premature translation termination codon in the presence and absence of the lead compound. Both the in vitro and in vivo nonsense suppression assays used herein and as described in International Patent Publication WO 01/44516, which is incorporated by reference herein in its entirety, can be used to identify lead compounds and can also be used to determine an $EC_{50}$ for the lead compounds.

Animal model systems can also be used to demonstrate the safety and efficacy of a compound of the invention. The compounds of the invention can be tested for biological activity using animal models for a disease, conditions or syndrome of interest. These include animals engineered to contain the target RNA element coupled to a functional readout system, such as a transgenic mouse.

Examples of animal models for cystic fibrosis include, but are not limited to, cftr(−/−) mice (see, e.g., Freedman et al., 2001, Gastroenterology 121(4):950-7), cftr(tm1HGU/tm1HGU) mice (see, e.g., Bernhard et al., 2001, Exp Lung Res 27(4):349-66), CFTR-deficient mice with defective cAMP-mediated Cl(−) conductance (see, e.g., Stotland et al., 2000, Pediatr Pulmonol 30(5):413-24), and C57BL/6-Cftr (m1UNC)/Cftr(m1UNC) knockout mice (see, e.g., Stotland et al., 2000, Pediatr Pulmonol 30(5):413-24).

Examples of animal models for muscular dystrophy include, but are not limited to, mouse, hamster, cat, dog, and *C. elegans*. Examples of mouse models for muscular dystrophy include, but are not limited to, the dy−/− mouse (see, e.g., Connolly et al., 2002, J Neuroimmunol 127(1-2):80-7), a muscular dystrophy with myositis (mdm) mouse mutation (see, e.g., Garvey et al., 2002, Genomics 79(2):146-9), the mdx mouse (see, e.g., Nakamura et al., 2001, Neuromuscul Disord 11(3):251-9), the utrophin-dystrophin knockout (dko) mouse (see, e.g., Nakamura et al., 2001, Neuromuscul Disord 11 (3):251-9), the dy/dy mouse (see, e.g., Dubowitz et al., 2000, Neuromuscul Disord 10(4-5):292-8), the mdx(Cv3) mouse model (see, e.g., Pillers et al., 1999, Laryngoscope 109(8):1310-2), and the myotonic ADR-MDX mutant mice (see, e.g., Kramer et al., 1998, Neuromuscul Disord 8(8):542-50). Examples of hamster models for muscular dystrophy include, but are not limited to, sarcoglycan-deficient hamsters (see, e.g., Nakamura et al., 2001, Am J Physiol Cell Physiol 281(2):C690-9) and the BIO 14.6 dystrophic hamster (see, e.g., Schlenker & Burbach, 1991, J Appl Physiol 71(5):1655-62). An example of a feline model for muscular dystrophy includes, but is not limited to, the hypertrophic feline muscular dystrophy model (see, e.g., Gaschen & Burgunder, 2001, Acta Neuropathol (Berl) 101(6):591-600). Canine models for muscular dystrophy include, but are not limited to, golden retriever muscular dystrophy (see, e.g., Fletcher et al., 2001, Neuromuscul Disord 11(3):239-43) and canine X-linked muscular dystrophy (see, e.g., Valentine et al., 1992, Am J Med Genet 42(3):352-6). Examples of *C. elegans* models for muscular dystrophy are described in Chamberlain & Benian, 2000, Curr Biol 10(21):R795-7 and Culette & Sattelle, 2000, Hum Mol Genet 9(6):869-77.

Examples of animal models for familial hypercholesterolemia include, but are not limited to, mice lacking functional LDL receptor genes (see, e.g., Aji et al., 1997, Circulation 95(2):4307), Yoshida rats (see, e.g., Fantappie et al., 1992, Life Sci 50(24):1913-24), the JCR:LA-cp rat (see, e.g., Richardson et al., 1998, Atherosclerosis 138(1):135-46), swine (see, e.g., Hasler-Rapacz et al., 1998, Am J Med Genet 76(5): 379-86), and the Watanabe heritable hyperlipidaemic rabbit (see, e.g., Tsutsumi et al., 2000, Arzneimittelforschung 50(2): 118-21; Harsch et al., 1998, Br J Pharmacol 124(2):227-82; and Tanaka et al., 1995, Atherosclerosis 114(1):73-82).

An example of an animal model for human cancer in general includes, but is not limited to, spontaneously occurring tumors of companion animals (see, e.g. Vail & MacEwen, 2000, Cancer Invest 18(8):781-92). Examples of animal models for lung cancer include, but are not limited to, lung cancer animal models described by Zhang & Roth (1994, In Vivo 8(5):755-69) and a transgenic mouse model with disrupted p53 function (see, e.g., Morris et al., 1998, J La State Med Soc 150(4):179-85). An example of an animal model for breast cancer includes, but is not limited to, a transgenic mouse that overexpresses cyclin D1 (see, e.g., Hosokawa et al., 2001, Transgenic Res 10(5):471-8). An example of an animal model for colon cancer includes, but is not limited to, a TCRbeta and p53 double knockout mouse (see, e.g., Kado et al., 2001, Cancer Res 61(6):2395-8). Examples of animal models for pancreatic cancer include, but are not limited to, a metastatic model of Panc02 murine pancreatic adenocarcinoma (see, e.g., Wang et al., 2001, Int J Pancreatol 29(1): 3746) and nu-nu mice generated in subcutaneous pancreatic tumours (see, e.g., Ghaneh et al., 2001, Gene Ther 8(3):199-208). Examples of animal models for non-Hodgkin's lymphoma include, but are not limited to, a severe combined immunodeficiency ("SCID") mouse (see, e.g., Bryant et al., 2000, Lab Invest 80(4):553-73) and an IgHmu-HOX11 transgenic mouse (see, e.g., Hough et al., 1998, Proc Natl Acad Sci USA 95(23):13853-8). An example of an animal model for esophageal cancer includes, but is not limited to, a mouse transgenic for the human papillomavinis type 16 E7 oncogene (see, e.g., Herber et al., 1996, J Virol 70(3):1873-81). Examples of animal models for colorectal carcinomas include, but are not limited to, Apc mouse models (see, e.g., Fodde & Smits, 2001, Trends Mol Med 7(8):369-73 and Kuraguchi et al., 2000, Oncogene 19(50):575-563). An example of an animal model for neurofibromatosis includes, but is not limited to, mutant NF1 mice (see, e.g., Cichowski et al., 1996, Semin Cancer Biol 7(5):291-8). Examples of animal models for retinoblastoma include, but are not limited to, transgenic mice that expression the simian virus 40 T antigen in the retina (see, e.g. Howes et al., 1994, Invest Ophthalmol Vis Sci 35(2):342-51 and Windle et al, 1990, Nature 343 (6259):665-9) and inbred rats (see, e.g., Nishida et al., 1981, Curr Eye Res 1(1):53-5 and Kobayashi et al., 1982, Acta Neuropathol (Berl) 57(2-3):203-8). Examples of animal models for Wilm's tumor include, but are not limited to, a WT1 knockout mice (see, e.g., Scharnhorst et al., 1997, Cell Growth Differ 8(2):133-43), a rat subline with a high incidence of neuphroblastoma (see, e.g., Mesfin & Breech, 1996, Lab Anim Sci 46(3):321-6), and a Wistar/Furth rat with Wilms' tumor (see, e.g., Murphy et al., 1987, Anticancer Res 7(4B):717-9).

Examples of animal models for retinitis pigmentosa include, but are not limited to, the Royal College of Surgeons ("RCS") rat (see, e.g., Vollrath et al., 2001, Proc Natl Acad Sci USA 98(22);12584-9 and Hanitzsch et al., 1998, Acta Anat (Basel) 162(2-3):119-26), a rhodopsin knockout mouse (see, e.g., Jaissle et al., 2001, Invest Ophthalmol Vis Sci 42(2):506-13), and Wag/Rij rats (see, e.g., Lai et al., 1980, Am J Pathol 98(1):281-4).

Examples of animal models for cirrhosis include, but are not limited to, $CCl_4$-exposed rats (see, e.g., Kloehn et al., 2001, Horm Metab Res 33(7):394-401) and rodent models instigated by bacterial cell components or colitis (see, e.g., Vierling, 2001, Best Pract Res Clin Gastroenterol 15(4):591-610).

Examples of animal models for hemophilia include, but are not limited to, rodent models for hemophilia A (see, e.g., Reipert et al., 2000, Thromb Haemost 84(5):826-32; Jarvis et al., 1996, Thromb Haemost 75(2):318-25; and Bi et al., 1995, Nat Genet 10(1):119-21), canine models for hemophilia A (see, e.g., Gallo-Penn et al., 1999, Hum Gene Ther 10(11): 1791-802 and Connelly et al, 1998, Blood 91(9);3273-81), murine models for hemophilia B (see, e.g., Snyder et al., 1999, Nat Med 5(1):64-70; Wang et al., 1997, Proc Natl Acad Sci USA 94(21):11563-6; and Fang et al., 1996, Gene Ther 3(3):217-22), canine models for hemophilia B (see, e.g., Mount et al., 2002, Blood 99(8):2670-6; Snyder et al., 1999, Nat Med 5(1):6470; Fang et al., 1996, Gene Ther 3(3):217-22); and Kay et al., 1994, Proc Natl Acad Sci USA 91(6): 2353-7), and a rhesus macaque model for hemophilia B (see, e.g., Lozier et al., 1999, Blood 93(6):1875-81).

Examples of animal models for von Willebrand disease include, but are not limited to, an inbred mouse strain RIIIS/J (see, e.g., Nichols et al., 1994, 83(11):3225-31 and Sweeney et al., 1990, 76(11):2258-65), rats injected with botrocetin (see, e.g., Sanders et al., 1988, Lab Invest 59(4):443-52), and porcine models for von Willebrand disease (see, e.g., Nichols et al., 1995, Proc Natl Acad Sci USA 92(7):2455-9; Johnson & Bowie, 1992, J Lab Clin Med 120(4):553-8); and Brinkhous et al., 1991, Mayo Clin Proc 66(7):733-42).

Examples of animal models for b-thalassemia include, but are not limited to, murine models with mutations in globin genes (see, e.g., Lewis et al., 1998, Blood 91(6):2152-6; Raja et al., 1994, Br J Haematol 86(1):156-62; Popp et al., 1985, 445:432-44; and Skow et al., 1983, Cell 34(3):1043-52).

Examples of animal models for kidney stones include, but are not limited to, genetic hypercalciuric rats (see, e.g., Bushinsky et al., 1999, Kidney Int 55(1):234-43 and Bushinsky et al., 1995, Kidney Int 48(6):1705-13), chemically treated rats (see, e.g., Grases et al., 1998, Scand J Urol Nephrol 32(4): 261-5; Burgess et al., 1995, Urol Res 23(4):239-42; Kumar et al., 1991, J Urol 146(5):1384-9; Okada et al., 1985, Hinyokika Kiyo 31(4):565-77; and Bluestone et al., 1975, Lab Invest 33(3):273-9), hyperoxaluric rats (see, e.g., Jones et al., 1991, J Urol 145(4):868-74), pigs with unilateral retrograde flexible nephroscopy (see, e.g., Seifinah et al., 2001, 57(4): 832-6), and rabbits with an obstructed upper urinary tract (see, e.g., Itatani et al., 1979, Invest Urol 17(3):234-40).

Examples of animal models for ataxia-telangiectasia include, but are not limited to, murine models of ataxia-telangiectasia (see, e.g., Barlow et al., 1999, Proc Natl Acad Sci USA 96(17):9915-9 and Inoue et al., 1986, Cancer Res 46(8):3979-82).

Examples of animal models for lysosomal storage diseases include, but are not limited to, mouse models for mucopolysaccharidosis type VII (see, e.g., Brooks et al., 2002, Proc Natl Acad Sci USA. 99(9):6216-21; Monroy et al., 2002, Bone 30(2):352-9; Vogler et al., 2001, Pediatr Dev Pathol. 4(5):421-33; Vogler et al., 2001, Pediatr Res. 49(3):342-8; and Wolfe et al., 2000, Mol Ther. 2(6):552-6), a mouse model for metachromatic leukodystrophy (see, e.g., Matzner et al., 2002, Gene Ther. 9(1):53-63), a mouse model of Sandhoff disease (see, e.g. Sango et al., 2002, Neuropathol Appl Neurobiol. 28(1):23-34), mouse models for mucopolysaccharidosis type III A (see, e.g., Bhattacharyya et al., 2001, Glycobiology 11(1):99-10 and Bhaumik et al., 1999, Glycobiology 9(12):1389-96.), arylsulfatase A (ASA)-deficient mice (see, e.g., D'Hooge et al., 1999, Brain Res. 847(2):3526 and D'Hooge et al, 1999, Neurosci Lett. 273(2):93-6); mice with an aspartylglucosaminuria mutation (see, e.g., Jalanko et al., 1998, Hum Mol Genet. 7(2):265-72); feline models of mucopolysaccharidosis type VI (see, e.g., Crawley et al., 1998, J Clin Invest. 101(1):109-19 and Norrdin et al., 1995, Bone 17(5):485-9); a feline model of Niemann-Pick disease type C (see, e.g., March et al., 1997, Acta Neuropathol (Berl). 94(2): 164-72); acid sphingomyelinase-deficient mice (see, e.g., Otterbach & Stoffel, 1995, Cell 81(7):1053-6), and bovine mannosidosis (see, e.g., Jolly et al., 1975, Birth Defects Orig Arctic Ser. 11(6):273-8).

Examples of animal models for tuberous sclerosis ("TSC") include, but are not limited to, a mouse model of TSC1 (see, e.g., Kwiatkowski et al., 2002, Hum Mol Genet. 11(5):525-34), a Tsc1 (TSC1 homologue) knockout mouse (see, e.g., Kobayashi et al., 2001, Proc Natl Acad Sci USA. 2001 Jul. 17;98(15):8762-7), a TSC2 gene mutant(Eker) rat model (see, e.g., Hino 2000, Nippon Rinsho 58(6):1255-61; Mizuguchi et al., 2000, J Neuropathol Exp Neurol. 59(3): 188-9; and Hino et al., 1999, Prog Exp Tumor Res. 35:95-108); and Tsc2(+/−) mice (see, e.g., Onda et al., 1999, J Clin Invest. 104(6):687-95).

4.3 Synthesis and Preparation

The compounds of the invention can be obtained via standard, well-known synthetic methodology, see e.g., March, J. Advanced Organic Chemistry; Reactions Mechanisms, and Structure, 4th ed., 1992. Starting materials useful for preparing the compounds of the invention and intermediates therefore, are commercially available or can be prepared from commercially available materials using known synthetic methods and reagents.

Compounds of formula I can be prepared as shown in Scheme A. An amine compound A1 is allowed to react with compound A2, wherein G represents a leaving group such as chloro, bromo, iodo or trifluoromethanesulfonyl. The reaction is usually performed in the presence of a basic reagent, e.g., triethylamine or pyridine, in a solvent such as methanol or dimethylformamide, and at temperatures ranging from about ambient to the reflux temperature of the chosen solvent. Alternatively, compounds of the invention, particularly compounds of formula I may be prepared by using reagents having the reversed substitution pattern. A compound A3, wherein L is an appropriate leaving group such as bromo or acetoxy is reacted with an amine A4, usually in the presence of an appropriate base and solvent and at temperatures from about ambient to reflux. The starting compounds A1-A4 for the preparation of compounds of the invention including compounds of formula I can be obtained commercially or can be prepared by methods familiar to one skilled in the art of organic synthesis.

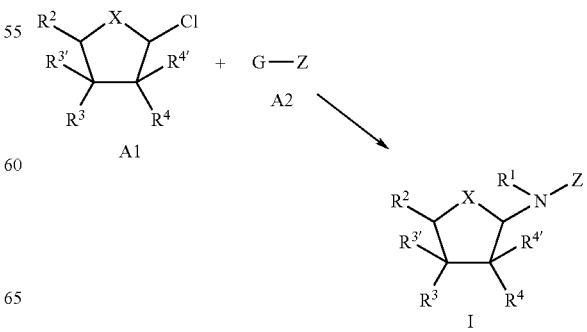

Scheme A

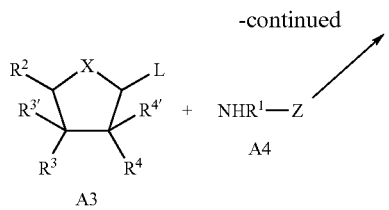

Compounds of formula II can be prepared as outlined in Scheme B. In one embodiment, a compound of formula B1, which possesses leaving groups G similar to that described in Scheme A, is allowed to react with $Y^2$ resulting in an intermediate of formula B2. This intermediate can then react with a compound of formula A1 as described in Scheme A to yield a compound of formula II. Inversely, a compound of formula B1 can be treated first with compound of formula A1 resulting in intermediate of formula B3 which is then allowed to react with $Y^2$ to afford formula II. The starting compounds of formula B1 are commercially available or can be easily prepared by methods familiar to one skilled in the art.

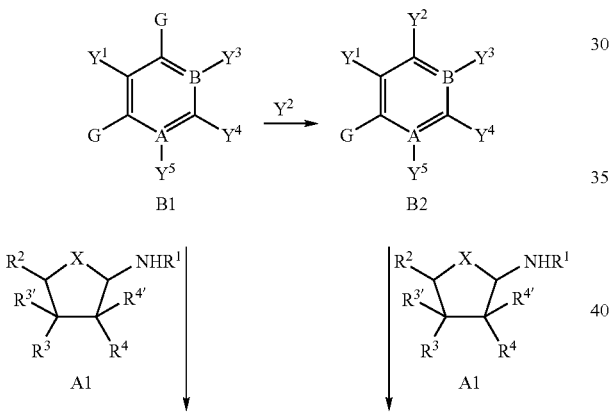

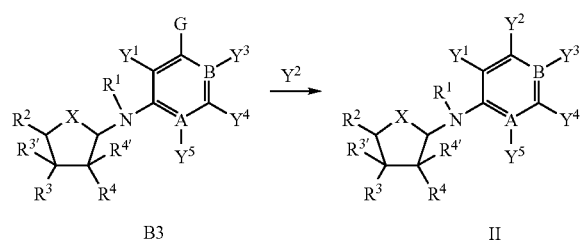

Compounds of formula VII can be prepared from compounds of formula C1 (Scheme C), wherein $P^1$, $P^2$ and $P^2$ can be suitable hydroxyl protecting groups that can be removed using protocols well established in the art of organic chemistry. A source describing hydroxyl protecting groups and their removal can be found in Greene and Wuts, Protective Groups in Organic Synthesis, $3^{rd}$ ed., pp 17-245, 1999, John Wiley & Sons, Inc., New York, N.Y. Representative hydroxyl groups include, but are not limited to, acetyl, benzoyl, benzyl, dimethylacetal and benzylidene. In the case where compound of formula A1 has $R^6=P^1$, $R^7=P^2$ and $R^8=P^3$, a compound of formula C1 can then be prepared as depicted in Scheme B.

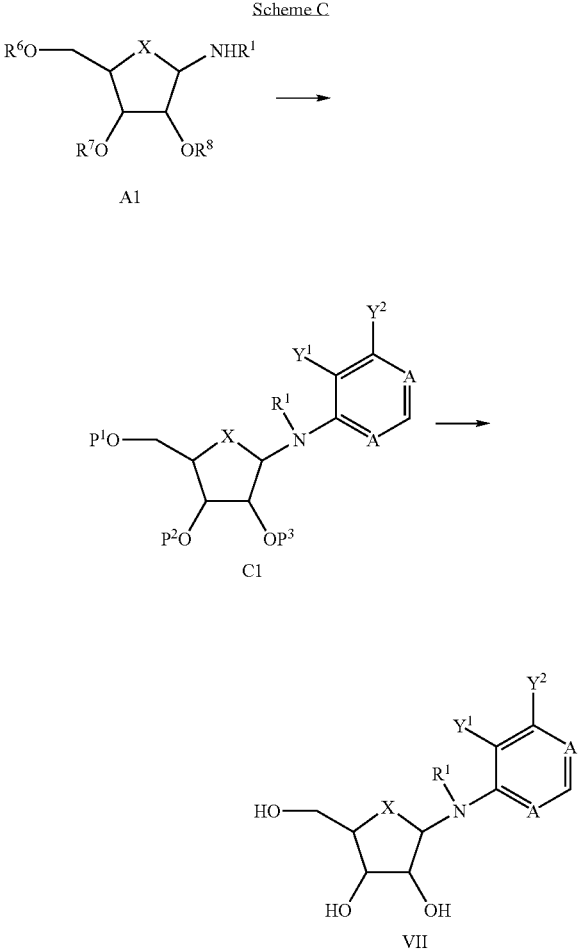

Compounds of formula D4 can be prepared as shown in Scheme D. Selective removal of protecting group P1 from compounds of formula C1 gives compounds of formula D1. Compounds of formula D1 can be converted to compounds of formula D2 by conversion of the hydroxyl group to a leaving group G, in which G can be groups such as, but not limited to, chloro, bromo, iodo, trifluoromethanesulonate, methanesulfonate or toluenesulfonate. Reaction of compounds of formula D2 with a nucleophile or metal hydride gives compounds of formula D3. Alternatively compounds of formula D1 can be converted to compounds of formula D3 (in which R=F) directly by treatment with a fluorinating reagent such as diethylamino sulfur trifluoride or related reagents as discussed in Organic Reactions, vol. 35, (1988), John Wiley & Sons, Inc., New York, N.Y. or by utilizing the Mitsunobu reaction as discussed in Organic Reactions, vol. 42, (1992), John Wiley & Sons, Inc., New York, N.Y. Removal of the protecting groups give compounds of formula D4.

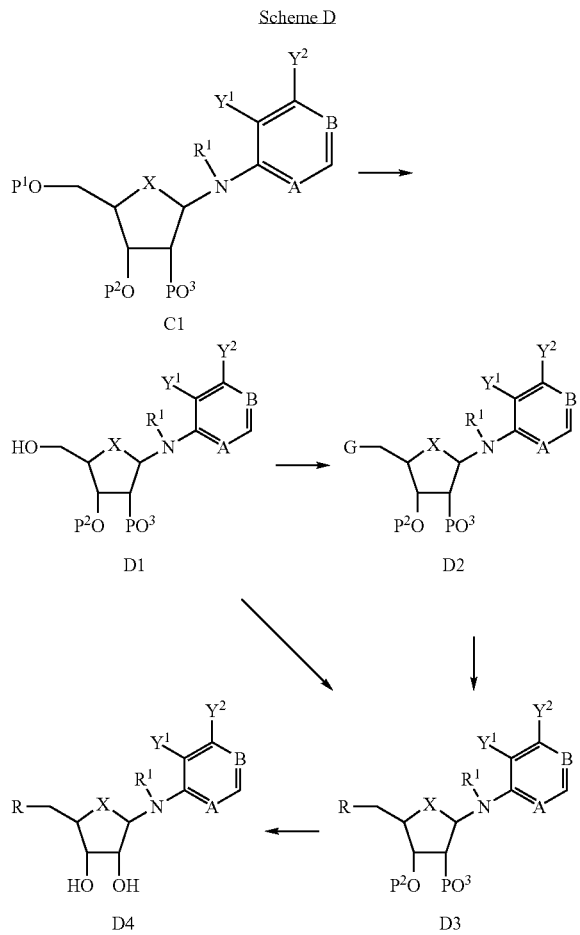

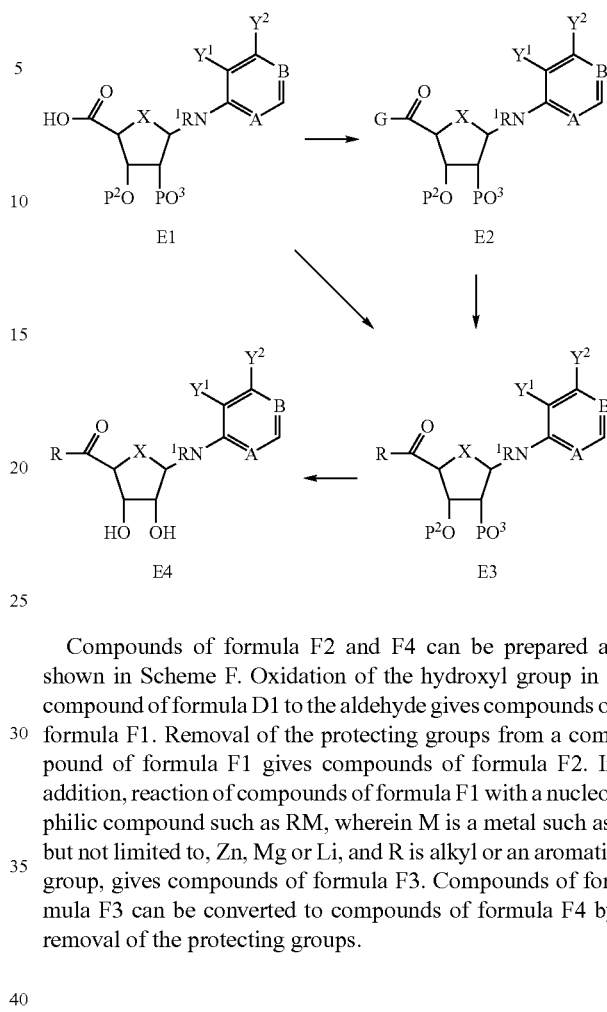

Compounds of formula E4 can be prepared as shown in Scheme E. The hydroxyl group in compounds of formula D1 can be oxidized to carboxylic acids of formula E1 which can be converted to activated compounds of formula E2 in which G is a leaving group such as, but not limited to, chloro, fluoro or bromo. Reaction of compounds of formula E2 with nucleophiles gives compounds of formula E3. Alternatively, compounds of formula E3 can be prepared directly from compounds of formula E1 by methods familiar to one skilled in the art. Removal of the protecting groups gives compounds of formula E4.

Compounds of formula F2 and F4 can be prepared as shown in Scheme F. Oxidation of the hydroxyl group in a compound of formula D1 to the aldehyde gives compounds of formula F1. Removal of the protecting groups from a compound of formula F1 gives compounds of formula F2. In addition, reaction of compounds of formula F1 with a nucleophilic compound such as RM, wherein M is a metal such as, but not limited to, Zn, Mg or Li, and R is alkyl or an aromatic group, gives compounds of formula F3. Compounds of formula F3 can be converted to compounds of formula F4 by removal of the protecting groups.

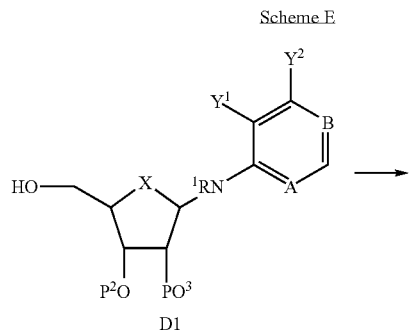

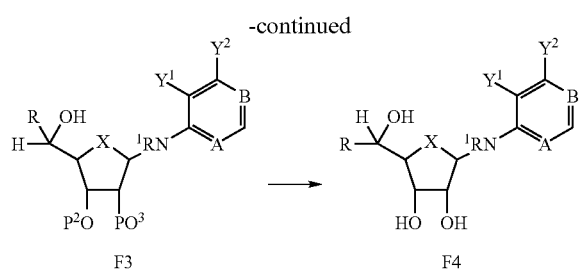

Compounds of formula G4 and G6 can be prepared as shown in scheme G. The protecting group P2 can be removed selectively to give the compounds of formula G1, which can be oxidized to give compounds of formula G2. Compounds of formula G2 can be fluorinated with a fluorinating reagent such as diethylaminosulfur trifluoride to give the difluorinated compounds of formula G5, which upon removal of the protecting groups can give compounds of formula G6. Alternatively compounds of formula G1 can be fluorinated with a fluorinating reagent such as diethylaminosulfur trifluoride to give compounds of formula G3 which upon removal of the protecting groups gives compounds of formula G4.

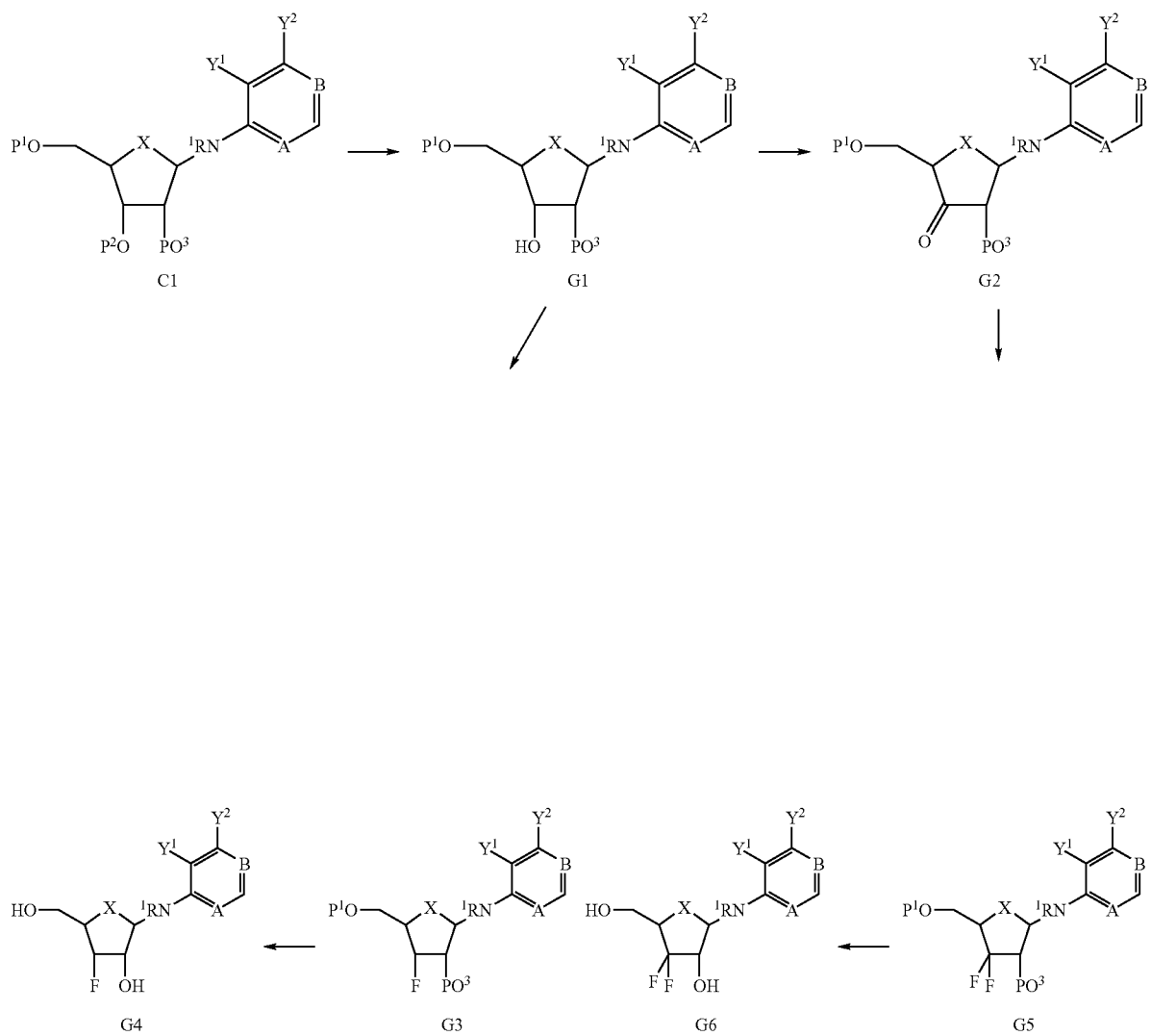

Compounds of formula H4 and H6 can be prepared as shown in scheme H. The protecting group P3 can be removed selectively to give the compounds of formula H1, which can be oxidized to give compounds of formula H2. Compounds of formula H2 can be fluorinated with a fluorinating reagent such as diethylaminosulfur trifluoride to give the difluorinated compounds of formula H5, which upon removal of the protecting groups can give compounds of formula H6. Alternatively, compounds of formula H1 can be fluorinated with a fluorinating reagent such as diethylaminosulfur trifluoride to give compounds of formula H3, which upon removal of the protecting groups gives compounds of formula H4.

sents a thioacyl group. Reaction of the thioacyl compounds of formula J2 following literature procedure such as given in Barton et al., Tetrahedron Lett. 3381 (1993), give compounds of formula J2 which upon removal of protecting groups gives compounds of formula J3. Compounds of formula 36 can be prepared from compounds of formula J2 by removal of protecting group P2 to give compounds of formula J4. Conversion of the hydroxyl group in compounds of formula J4 to a leaving group G in which G can be groups such as, but not limited to, chloro, bromo, iodo, trifluoromethanesulonate, methanesulfonate and toluenesulfonate can give compounds

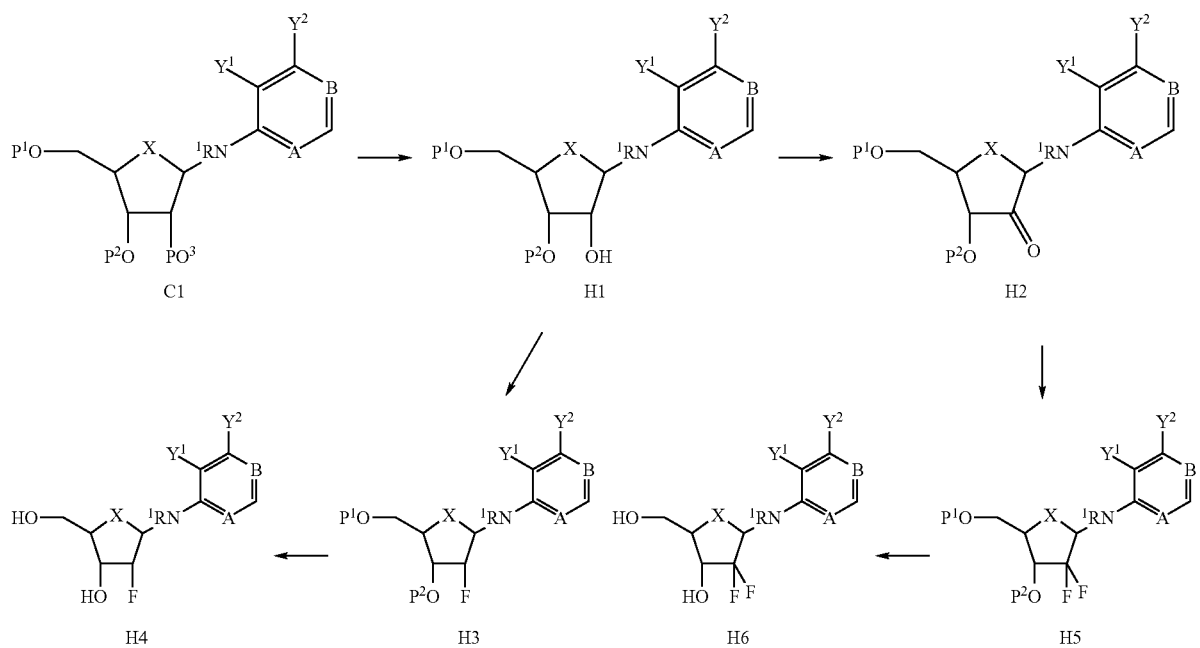

Scheme H

Compounds of the formula J3 and J6 can be prepared as shown in Scheme J. The hydroxyl group in H1 can be thioacylated to give compounds of formula J2 in which T represents of formula J5. Treatment of the compounds of formula J5 with a base such as DBU followed by removal of the protecting group can give compounds of formula J6.

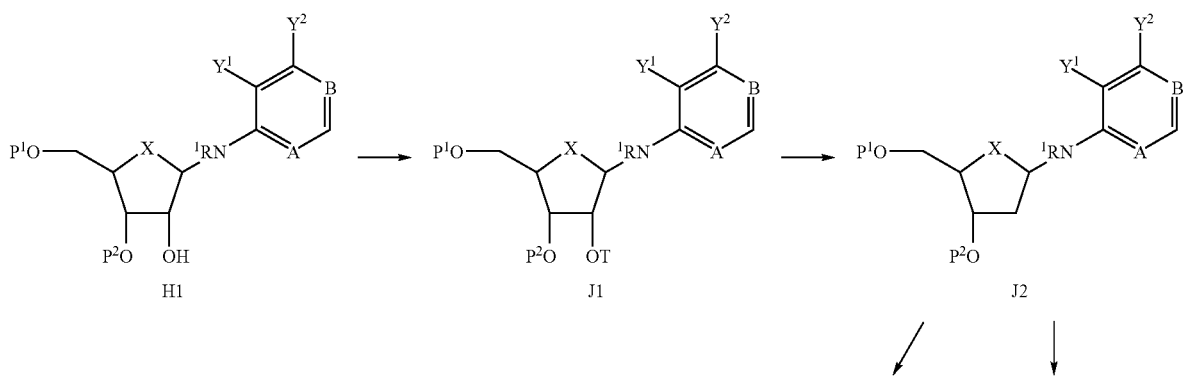

Scheme J

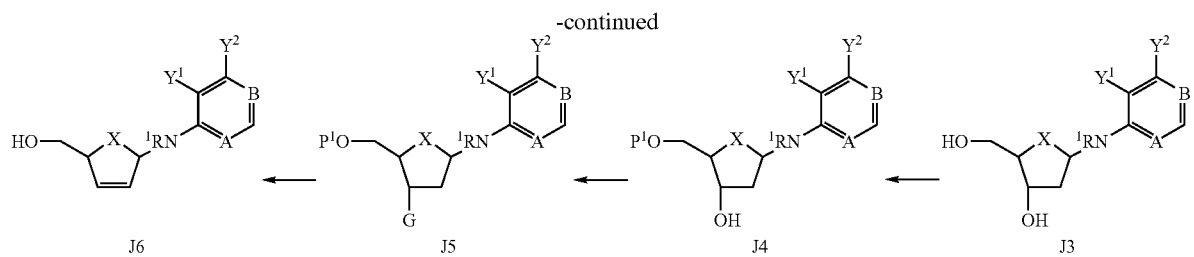

J6   J5   J4   J3

Compounds of formula K3 can be prepared as shown in scheme K. Compounds of formula K1 can be obtained as outlined in Iwakawa et al., Carbohydrate Research 121:99 (1983). Reaction of compounds of formula K1 with the amino substituted reactant can give compounds of formula K2 as described in Paquette et al. ed., Organic Reactions, vol. 55, (2000). Removal of protecting groups in compounds of formula K2 can give compounds of formula K3.

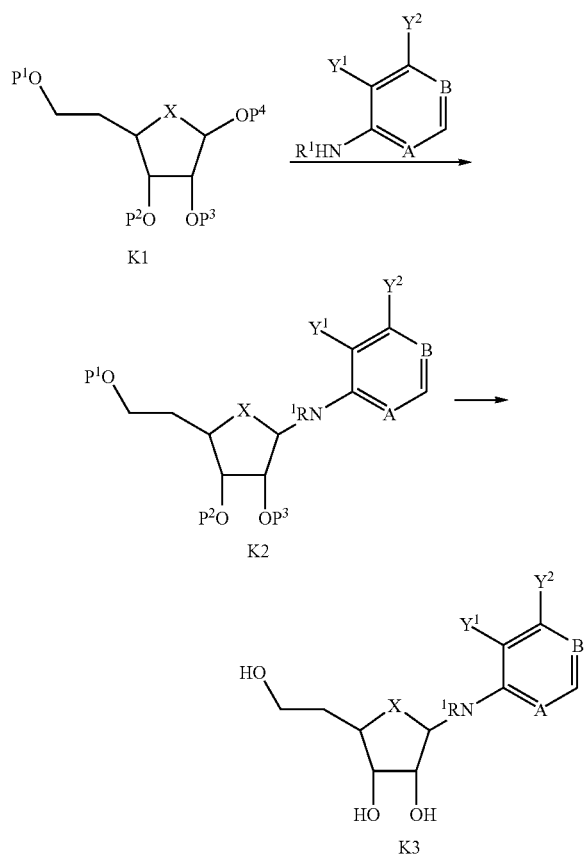

Scheme K

Compounds of the invention can also be synthesized using the syntheses described in Moss et. al., J. Med. Chem. 31:786-790 (1988); Kamikawa et. al., J. Chem. Soc. Chem. Commun. 195 (1988); Lee et. al., Bioorg. And Med. Chem. Lett. 11:293-301 (2001); Nogueras et. al., Nucleosides and Nucleotides 13: 447-457 (1994); Burgdorf et. al. Chem. Eur. J. 8:293-301 (2002); Mabry et. al., Nucleosides and Nucleotides 13:1125-1133 (1994); Palmer et. al., Tet. Lett. 31:279-282 (1990); Baxter et. al., Nucleosides and Nucleotides 10:393-396 (1991); Franchetti et al. Nucleosides and Nucleotides 10:543-545 (1991) and Organic Reactions, vol. 55, (2000), Paquette et al. ed., each of which is incorporated by reference herein in its entirety.

4.4 Methods of Use

The invention encompasses methods of treating and preventing diseases or disorders ameliorated by the suppression of premature translation termination and/or nonsense-mediated mRNA decay in a patient which comprise administering to a patient in need of such treatment or prevention a therapeutically effective amount of a compound of the invention.

In one embodiment, the present invention encompasses the treatment or prevention of any disease which is associated with a gene exhibiting premature translation termination and/or nonsense-mediated mRNA decay. In one embodiment, the disease is due, in part, to the lack of or reduced expression of the gene resulting from a premature stop codon. Specific examples of genes which may exhibit premature translation termination and/or nonsense-mediated mRNA decay and diseases associated with premature translation termination and/or nonsense-mediated mRNA decay are found in U.S. Provisional Patent Application No. 60/390,747, titled: Methods For Identifying Small Molecules That Modulate Premature Translation Termination And Nonsense Mediated mRNA Decay, filed Jun. 21, 2002, and International Application PCT/US03/19760, filed Jun. 23, 2003, both of which are incorporated herein by reference in their entirety.

Diseases ameliorated by the suppression of premature translation termination and/or nonsense-mediated mRNA decay include, but are not limited to: cancers, autoimmune diseases, blood diseases, collagen diseases, diabetes, neurodegenerative diseases, proliferative diseases, cardiovascular diseases, pulmonary diseases, inflammatory diseases or central nervous system diseases.

Specific diseases associated with a genetic nonsense mutation which are within the scope of the methods of the invention include, but are not limited to, amyloidosis, hemophilia, Alzheimer's disease, Tay Sachs disease, Niemann Pick disease, atherosclerosis, giantism, dwarfism, hypothyroidism, hyperthyroidism, aging, obesity, Parkinson's disease, cystic fibrosis, muscular dystrophy, heart disease, kidney stones, ataxia-telangiectasia, familial hypercholesterolemia, retinitis pigmentosa, Duchenne muscular dystrophy, and Marfan syndrome. In one embodiment, the diseases are associated with a genetic mutation.

In one embodiment, the compounds of the invention are useful for treating or preventing an autoimmune disease caused by a genetic nonsense mutation. In a preferred embodiment, the autoimmune disease is rheumatoid arthritis or graft versus host disease.

In another embodiment, the compounds of the invention are useful for treating or preventing a blood disease caused by a genetic nonsense mutation. In a preferred embodiment, the blood disease is hemophilia, Von Willebrand disease, ataxia-telangiectasia, β-thalassemia or kidney stones.

In another embodiment, the compounds of the invention are useful for treating or preventing a collagen disease caused by a genetic nonsense mutation. In a preferred embodiment, the collagen disease is osteogenesis imperfecta or cirrhosis.

In another embodiment, the compounds of the invention are useful for treating or preventing diabetes caused by a genetic nonsense mutation.

In another embodiment, the the compounds of the invention are useful for treating or preventing an inflammatory disease caused by a genetic nonsense mutation. In a preferred embodiment, the inflammatory disease is arthritis, rheumatoid arthritis or osteoarthritis.

In another embodiment, the compounds of the invention are useful for treating or preventing a central nervous system disease caused by a genetic nonsense mutation. In one embodiment the central nervous system disease is a neurodegenerative disease. In a preferred embodiment, the central nervous system disease is multiple sclerosis, muscular dystrophy, Duchenne muscular dystrophy, Alzheimer's disease, Tay Sachs disease, Niemann Pick disease, late infantile neuronal ceroid lipofuscinosis (LINCL) or Parkinson's disease.

In another embodiment, the compounds of the invention are useful for treating or preventing cancer caused by a genetic nonsense mutation. In one embodiment, the patient with cancer is a human. In a preferred embodiment, the cancer is of the head and neck, eye, skin, mouth, throat, esophagus, chest, bone, blood, lung, colon, sigmoid, rectum, stomach, prostate, breast, ovaries, kidney, liver, pancreas, brain, intestine, heart or adrenals. In one embodiment, the cancer is a solid tumor. In one embodiment, the cancer is associated with a nonsense mutation. In another embodiment, the cancer is associated with a genetic nonsense mutation.

In other embodiments, diseases to be treated or prevented by administering to a patient in need thereof an effective amount of a compound of the invention include, but are not limited to, solid tumors such as sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pineloma, hemangioblastoma, acoustic neuroma, oligodendroglioma, menangioma, melanoma, neuroblastoma and retinoblastoma In another embodiment, diseases to be treated or prevented by administering to a patient in need thereof an effective amount of a compound of the invention include, but are not limited to, a blood-born tumor such as acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia, chronic lymphocytic leukemia, hairy cell leukemia, or multiple myeloma See e.g., Harrison's Principles of Internal Medicine, Eugene Braunwald et al., eds., pp. 491-762 (15th ed. 2001).

In yet another embodiment, the invention encompasses treatment of a human afflicted with a solid tumor or a blood tumor.

In a preferred embodiment, the invention encompasses a method of treating or preventing a disease ameliorated by modulation of premature translation termination and/or nonsense-mediated mRNA decay, or ameliorating one or more symptoms associated therewith comprising contacting a cell with an effective amount of a compound of the invention. Cells encompassed by the present methods include animal cells, mammalian cells, bacterial cells, plant cells and virally infected cells. In one embodiment, the nonsense mutation is a genetic mutation (i.e., the nonsense codon was present in the progenitor DNA).

In certain embodiments, a compound of the invention is administered to a patient, preferably a mammal, more preferably a human, as a preventative measure against a disease associated with premature translation termination and/or nonsense-mediated mRNA decay.

In a preferred embodiment, it is first determined that the patient is suffering from a disease associate with premature translation termination and/or nonsense-mediated mRNA decay. In another embodiment, the patient has undergone a screening process to determine the presence of a nonsense mutation comprising the steps of screening a subject, or cells extracted therefrom, by an acceptable nonsense mutation screening assay. In a preferred embodiment, the DNA of the patient can be sequenced or subjected to Southern Blot, polymerase chain reaction (PCR), use of the Short Tandem Repeat (STR), or polymorphic length restriction fragments (RFLP) analysis to determine if a nonsense mutation is present in the DNA of the patient. In one embodiment, it is determined whether the nonsense mutation is a genetic mutation by comparison of progenitor DNA. Alternatively, it can be determined if altered levels of the protein with the nonsense mutation are expressed in the patient by western blot or other immunoassays. In another embodiment, the patient is an unborn child who has undergone screening in utero for the presence of a nonsense mutation. Administration of a compound of the invention can occur either before or after birth. In a related embodiment, the therapy is personalized in that the patient is screened for a nonsense mutation screening assay and treated by the administration of one or more compounds of the invention; particularly, the patient may be treated with a compound particularly suited for the mutations in question; e.g., depending upon the disease type, cell type, and the gene in question. Such methods are well known to one of skill in the art.

In another embodiment, the cells (e.g., animal cells, mammalian cells, bacterial cells, plant cells and virally infected cells) are screened for premature translation termination and/or nonsense-mediated mRNA decay with a method such as that described above (i.e., the DNA of the cell can be sequenced or subjected to Southern Blot, polymerase chain reaction (PCR), use of the Short Tandem Repeat (STR), or polymorphic length restriction fragments (RFLP) analysis to determine if a nonsense mutation is present in the DNA of the cell).

Specific methods of the invention further comprise the administration of an additional therapeutic agent (i.e., a therapeutic agent other than a compound of the invention). In certain embodiments of the present invention, the compounds of the invention can be used in combination with at least one other therapeutic agent. Therapeutic agents include, but are not limited to non-opioid analgesics; non-steroid anti-inflammatory agents; antiemetics; β-adrenergic blockers; anticonvulsants; antidepressants; $Ca^{2+}$-channel blockers; anticancer agent and mixtures thereof.

In certain embodiments, the compounds of the invention can be administered or formulated in combination with anticancer agents. Suitable anticancer agents include, but are not limited to: alkylating agents; nitrogen mustards; folate antagonists; purine antagonists; pyrimidine antagoinists; spindle poisons; topoisomerase inhibitors; apoptosis inducing agents; angiogenesis inhibitors; podophyllotoxins; nitrosoureas; cisplatin; carboplatin; interferon; asparginase; tamoxifen; leuprolide; flutamide; megestrol; mitomycin; bleomycin; doxorubicin; irinotecan and taxol.

In certain embodiments, the compounds of the invention can be administered or formulated in combination with antibiotics. In certain embodiments, the antibiotic is a macrolide (e.g., tobramycin), a cephalosporin (e.g., cephalexin, cephradine, cefuroxime, cefprozil, cefaclor, cefixime or cefadroxil), a clarithromycin (e.g., clarithromycin), an erthromycin (e.g., erythromycin), a penicillin (e.g., penicillin V) or a quinolone (e.g., ofloxacin, ciprofloxacin or norfloxacin). In a preferred embodiment, the antibiotic is active against *Pseudomonas aeruginosa*.

The compounds of the invention and the other therapeutics agent can act additively or, more preferably, synergistically. In a preferred embodiment, a composition comprising a compound of the invention is administered concurrently with the administration of another therapeutic agent, which can be part of the same composition or in a different composition from that comprising the compounds of the invention. In another embodiment, a compound of the invention is administered prior to or subsequent to administration of another therapeutic agent.

The magnitude of a prophylactic or therapeutic dose of a particular active ingredient of the invention in the acute or chronic management of a disease or condition will vary, however, with the nature and severity of the disease or condition, and the route by which the active ingredient is administered. The dose, and perhaps the dose frequency, will also vary according to the age, body weight, and response of the individual patient. Suitable dosing regimens can be readily selected by those skilled in the art with due consideration of such factors. In general, the recommended daily dose range for the conditions described herein lie within the range of from about 0.1 mg to about 2000 mg per day. In one embodiment, the compound of the invention is given as a single once-a-day dose. In another embodiment, the compound of the invention is given as divided doses throughout a day. More specifically, the daily dose is administered in a single dose or in equally divided doses. Preferably, a daily dose range should be from about 5 mg to about 500 mg per day, more preferably, between about 10 mg and about 200 mg per day. In managing the patient, the therapy should be initiated at a lower dose, perhaps about 1 mg to about 25 mg, and increased if necessary up to about 200 mg to about 2000 mg per day as either a single dose or divided doses, depending on the patient's global response.

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

The phrases "therapeutically effective amount", "prophylactically effective amount" and "therapeutically or prophylactically effective amount," as used herein encompass the above described dosage amounts and dose frequency schedules. Different therapeutically effective amounts may be applicable for different diseases and conditions, as will be readily known by those of ordinary skill in the art. Similarly, amounts sufficient to treat or prevent such diseases, but insufficient to cause, or sufficient to reduce, adverse effects associated with conventional therapies are also encompassed by the above described dosage amounts and dose frequency schedules.

4.5 Pharmaceutical Compositions

Pharmaceutical compositions and single unit dosage forms comprising a compound of the invention, or a pharmaceutically acceptable polymorph, prodrug, salt, solvate, hydrate, or clathrate thereof are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration Pharmaceutical compositions and dosage forms of the invention comprise a compound of the invention, or a pharmaceutically acceptable prodrug, polymorph, salt, solvate, hydrate, or clathrate thereof. Pharmaceutical compositions and dosage forms of the invention typically also comprise one or more pharmaceutically acceptable excipients.

A particular pharmaceutical composition encompassed by this embodiment comprises a compound of the invention, or a pharmaceutically acceptable polymorph, prodrug, salt, solvate, hydrate, or clathrate thereof, and at least one additional therapeutic agent. Examples of additional therapeutic agents include, but are not limited to: anti-cancer drugs and anti-inflammation therapies including, but not limited to, those listed above in Section 4.4.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of inflammation or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

This invention further encompasses anhydrous (e.g., <1% water) pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise a compound of the invention, or a pharmaceutically acceptable salt, solvate, clathrate, hydrate, polymoprh or prodrug thereof lie within the range of from about 0.1 mg to about 2000 mg per day, given as a single once-a-day dose in the morning but preferably as divided doses throughout the day taken with food. More preferably, the daily dose is administered twice daily in equally divided doses. Preferably, a daily dose range should be from about 5 mg to about 500 mg per day, more preferably, between about 10 mg and about 200 mg per day. In managing the patient, the therapy should be initiated at a lower dose, perhaps about 1 mg to about 25 mg, and increased if necessary up to about 200 mg to about 2000 mg per day as either a single dose or divided doses, depending on the patient's global response.

4.5.1. Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g. Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystaline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant. Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

4.5.2. Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

Controlled-release pharmaceutical products can improve drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.5.3. Parenteral Dosage Forms

Parenteral dosage forms can be administered to patients by various routes including, but not limited to, subcutaneous, intravenous (including bolus injection), intramuscular, and intra-arterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. For example, lyophilized sterile compositions suitable for reconstitution into particulate-free dosage forms suitable for administration to humans.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Parenteral dosage forms are preferred for the methods of preventing, treating or managing disease in a cancer patient 4.5.4. Transdermal and Topical Dosage Forms Transdermal and topical dosage forms of the invention include, but are not limited to, creams, lotions, ointments, gels, solutions, emulsions, suspensions, or other forms known to one of skill in the art. See, e.g., Remington's Pharmaceutical Sciences, 18th eds., Mack Publishing, Easton Pa. (1990); and Introduction to Pharmaceutical Dosage Forms, 4th ed., Lea & Febiger, Philadelphia (1985). Transdermal dosage forms include "reservoir type" or "matrix type"

patches, which can be applied to the skin and worn for a specific period of time to permit the penetration of a desired amount of active ingredients.

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 18th eds., Mack Publishing, Easton Pa. (1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

4.5.5. Mucosal Dosage Forms and Lung Delivery

Mucosal dosage forms of the invention include, but are not limited to, ophthalmic solutions, sprays and aerosols, or other forms known to one of skill in the art. See, e.g., Remington's Pharmaceutical Sciences, 18th eds., Mack Publishing, Easton Pa. (1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. In one embodiment, the aerosol comprises a carrier. In another embodiment, the aerosol is carrier free.

A compound of the invention can also be administered directly to the lung by inhalation (see e.g., Tong et al., PCT Application, WO 97/39745; Clark et al, PCT Application, WO 99/47196, which are herein incorporated by reference). For administration by inhalation, a compound of the invention can be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas can be used to deliver a compound of the invention directly to the lung. MDI devices are available from a number of suppliers such as 3M Corporation, Aventis, Boehlinger Ingleheim, Forest Laboratories, Glaxo-Wellcome, Schering Plough and Vectura.

Alternatively, a Dry Powder Inhaler (DPI) device can be used to administer a compound of the invention to the lung (See, e.g., Raleigh et al., Proc. Amer. Assoc. Cancer Research Annual Meeting, 1999, 40, 397, which is herein incorporated by reference). DPI devices typically use a mechanism such as a burst of gas to create a cloud of dry powder inside a container, which can then be inhaled by the patient. DPI devices are also well known in the art and can be purchased from a number of vendors which include, for example, Fisons, Glaxo-Wellcome, Inhale Therapeutic Systems, ML Laboratories, Qdose and Vectura A popular variation is the multiple dose DPI ("MDDPI") system, which allows for the delivery of more than one therapeutic dose. MDDPI devices are available from companies such as AtaZeneca, GlaxoWellcome, IVAX, Schering Plough, SkyePharma and Vectura For example, capsules and cartridges of gelatin for use in an inhaler or insufflator can be formulated containing a powder mix of the compound and a suitable powder base such as lactose or starch for these systems.

Another type of device that can be used to deliver a compound of the invention to the lung is a liquid spray device supplied, for example, by Aradigm Corporation. Liquid spray systems use extremely small nozzle holes to aerosolize liquid drug formulations that can then be directly inhaled into the lung.

In a preferred embodiment, a nebulizer device is used to deliver a compound of the invention to the lung. Nebulizers create aerosols from liquid drug formulations by using, for example, ultrasonic energy to form fine particles that can be readily inhaled (See e.g., Verschoyle et al., British J Cancer, 1999, 80, Suppl 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974, which are herein incorporated by reference), Aventis and Batelle Pulmonary Therapeutics. Inhaled compound of the invention, delivered by nebulizer devices, is currently under investigation as a treatment for aerodigestive cancer (Engelke et al., Poster 342 at American Association of Cancer Research, San Francisco, Calif., Apr. 1-5, 2000) and lung cancer (Dahl et al., Poster 524 at American Association of Cancer Research, San Francisco, Calif., Apr. 1-5, 2000).

In a particularly preferred embodiment, an electrohydrodynamic ("EHD") aerosol device is used to deliver a compound of the invention to the lung. EHD aerosol devices use electrical energy to aerosolize liquid drug solutions or suspensions (see e.g., Noakes et al., U.S. Pat. No. 4,765,539; Coffee, U.S. Pat. No. 4,962,885; Coffee, PCT Application, WO 94/12285; Coffee, PCT Application, WO 94/14543; Coffee, PCT Application, WO 95/26234, Coffee, PCT Application, WO 95/26235, Coffee, PCT Application, WO 95/32807, which are herein incorporated by reference). The electrochemical properties of the compound of the invention formulation may be important parameters to optimize when delivering this drug to the lung with an EHD aerosol device and such optimization is routinely performed by one of skill in the art EHD aerosol devices may more efficiently delivery drugs to the lung than existing pulmonary delivery technologies. Other methods of intra-pulmonary delivery of a compound of the invention will be known to the skilled artisan and are within the scope of the invention.

Liquid drug formulations suitable for use with nebulizers and liquid spray devices and EHD aerosol devices will typically include a compound of the invention with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of a compound of the invention. Preferably, this material is liquid such as an alcohol, glycol, polyglycol or a fatty acid. Other methods of formulating liquid drug solutions or suspension suitable for use in aerosol devices are known to those of skill in the art (See, e.g., Biesalski, U.S. Pat. No. 5,112,598; Biesalski, U.S. Pat. No. 5,556,611, which are herein incorporated by reference). A compound of the invention can also be formulated in rectal or vaginal compositions such as suppositories or retention enemas, e.g., containing conventional suppository bases such as cocoa butter or other glycerides.

In addition to the formulations described previously, a compound of the invention can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Alternatively, other pharmaceutical delivery systems can be employed. Liposomes and emulsions are well known examples of delivery vehicles that can be used to deliver a compound of the invention. Certain organic solvents such as dimethylsulfoxide can also be employed, although usually at the cost of greater toxicity. A compound of the invention can also be delivered in a controlled release system. In one embodiment, a pump can be used (Sefton, CRC Crit. Ref Biomed Eng., 1987, 14, 201; Buchwald et al., Surgery, 1980, 88, 507; Saudek et al., N. Engl. J. Med, 1989, 321, 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J Macromol. Sci. Rev. Macromol. Chem., 1983, 23, 61; see also Levy et al., Science 1985, 228, 190; During et al., Ann. Neurol., 1989, 25, 351; Howard et al., 1989, J. Neurosurg. 71, 105). In yet another embodiment, a controlled-release system can be placed in proximity of the target of the compounds of the invention, e.g., the lung, thus requiring only a fraction of the systemic dose (see, e.g., Goodson, in Medical Applications of Controlled Release, supra, vol. 2, pp. 115 (1984)). Other controlled-release system can be used (see e.g., Langer, Science, 1990, 249, 1527).

Suitable excipients (e.g., carriers and diluents) and other materials that can be used to provide mucosal dosage forms encompassed by this invention are well known to those skilled in the pharmaceutical arts, and depend on the particular site or method which a given pharmaceutical composition or dosage form will be administered. With that fact in mind, typical excipients include, but are not limited to, water, ethanol, ethylene glycol, propylene glycol, butane-1,3-diol, isopropyl myristate, isopropyl pannitate, mineral oil, and mixtures thereof, which are non-toxic and pharmaceutically acceptable. Examples of such additional ingredients are well known in the art. See, e.g., Remington's Pharmaceutical Sciences, 18th eds., Mack Publishing, Easton Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

5. EXAMPLES

5.1 Synthesis of Illustrative Compounds 5.1.1. Synthesis of 6-AMINO-5-NITRO-4-(β-D-RIBOFURANOSYLAMINO)-PYRIMIDINE (1)

A solution of 2',3'-O-Isopropylidene-β-D-ribofuranosylamine p-toluenesulfonate salt (2.65 g, 7.34 mmol) in 30 mL of N,N-dimethylformamide at room temperature was treated first with triethylamine (2.3 mL, 16.7 mmol) followed by the slow addition of 4,6-dichloro-5-nitropyrimidine (1.30 g, 6.68 mmol). After stirring for 3 h, the yellow solution was diluted with ethyl acetate (50 mL) and washed with water (50 mL). The aqueous phase was further extracted with 2×20 mL of ethyl acetate and the combined organic extracts were washed with 2×50 mL of brine, dried over $MgSO_4$, filtered and concentrated in vacuo. The resulting crude product was purified by silica gel chromatography (3:1 hexane/ethyl acetate) to afford 6-chloro-5-nitro-4-(2,3-O-isopropylidene-β-D-ribofuranosylamino)pyrimidine (1.37 g, 59%) as a white powder (m.p. 117-119° C.). TLC Rf 0.3 (3:1 hexane/ethyl acetate). $^1$H NMR ($CDCl_3$, 300 MHz): δ 8.71 (1H, d, J=8.7 Hz), 8.43 (1H, s), 6.35 (1H, d, J=8.7 Hz), 4.93 (1H, J=6.0 Hz), 4.69 (1H, d, J=6.0 Hz), 4.44 (1H, s), 3.88 (2H, dd, J=3.6 Hz, 1.8 Hz), 2.81 (1H, dd, J=2.4 Hz, 2.1 Hz), 1.57 (3H, s), 1.36 (3H, s). MS (ES+): 347.

To a solution of 6-chloro-5-nitro-4-(2',3'-O-isopropylidene-β-D-ribofuranosylamino)pyrimidine (760 mg, 2.19 mmol) in N,N dimethylformamide (20 mL) at room temperature was added a solution of 7N $NH_3$ in MeOH (626 μL, 4.38 mmol). The solution was stirred for 2 h and then diluted with 20 mL of ethyl acetate and washed with water. The aqueous layer was further extracted with 2×10 mL of ethyl acetate and the combined organic layers were washed with 2×20 mL of brine, dried over $MgSO_4$, filtered and concentrated in vacuo. The resulting crude product was purified by chromatography on silica gel (1:3 0:100 hexane/ethyl acetate) to yield 6-amino-5-nitro-4-(2,3-O-isopropylidene-β-D-ribofuranosylamino)pyrimidine (609 mg, 89%) as a slightly yellow solid. $^1$H NMR ($d_6$-DMSO, 300 MHz): δ 9.95 (1H, d, J=8.4 Hz), 8.54 (2H, s), 7.98 (1H, s), 6.21 (1H, d, J=8.4 Hz), 5.62 (1H, t, J=3.0 Hz), 4.80 (1H, d, J=6.0 Hz), 4.64 (1H, d, J=6.3 Hz), 4.23 (1H, s), 3.47-3.63 (2H, m), 1.44 (3H, s), 1.26 (3H, s). MS (ES+): 329.

Deprotection of the acetonide was accomplished by adding 5 mL of 9:1 TFA/$H_2O$ to 6-amino-5-nitro-4-(2',3'-O-isopropylidene-β-D-ribofuranosylamino)pyrimidine (538 mg, 1.64 mmol). The solution was stirred at room temperature for 10 minutes and then the solvent was removed in vacuo. The crude material was then triturated with diethyl ether and the resulting off-white solid was filtered to yield 360 mg (55%) of the desired 6-amino-5-nitro-4-(β-D-ribofuranosylamino)pyrimidine as the trifluoroacetate salt, as seen by $^{19}$F NMR (d$_6$-DMSO, 300 MHz): δ −75.5. $^1$H NMR (d$_6$-DMSO, 300 MHz): d 9.28 (1H, d, J=7.5 Hz), 8.57 (2H, s), 7.98 (1H, s), 5.76 (1H, dd, J=7.5 Hz, 3.3 Hz), 4.50 (6H, broad s), 4.06 (1H, dd, J=5.1 Hz), 3.91 (1H, dd, 3=3.6 Hz), 3.77 (1H, d, I=3.3 Hz, 2.1 Hz), 3.53 (1H, dd, J=11.7 Hz, 3.0 Hz), 3.43 (1H, dd, J=11.7 Hz, 2.4 Hz). MS (ES+): 288.

5.1.2. Synthesis of 6-(N-METHYLAMINO)-5-NITRO-4-(β-D-RIBOFURANOSYLAMINO)PYRIMIDINE (2)

To a solution of 6-chloro-5-nitro-4-(2',3'-O-isopropylidene-β-D-ribofuranosylamino)pyrimidine (200 mg, 0.577 mmol) in N,N-dimethylformamide (2 mL) at room temperature was added a 40% aqueous solution of N-methylamine (124 μL, 1.44 mmol). The solution was stirred for 4 h, diluted with 15 mL water and extracted with ethyl acetate (2×15 mL) and the combined organic layers were washed with brine (2×15 mL), dried over MgSO$_4$, filtered and concentrated in vacuo. The resulting crude product was deprotected following the procedure listed above for Acetonide Deprotection Step. The product was triturated with ether to give 131 mg of 6-(N-methylamino)-5-nitro-4-(β-D-ribofuranosylamino)pyrimidine as a yellow solid.

5.1.3. Synthesis of 5,6-DIAMINO-4-(β-D-RIBOFURANOSYLAMINO)PYRIMIDINE (3)

To a solution of 6-amino-5-nitro-4-(2',3'-O-isopropylidene-β-D-ribofuranosylamino)pyrimidine (50 mg, 0.153 mmol) in methanol (5 mL) was added 10% Pd/C (20 mg) and the mixture was hydrogenated at 50 psi for 4 hours at room temperature. The mixture was filtered through celite and the celite washed with methanol. The filtrate was concentrated to give 45 mg of the product as a brown oil. The product was deprotected following the procedure listed above for Acetonide Deprotection Step to give 5,6-diamino-4-(β-D-ribofuranosylamino)pyrimidine as a brown oil.

5.1.4. Synthesis of 3-nitro-2-(β-D-ribofuranosylamino) pyridine (4)

A solution of 2',3'-O-Isopropylidene-O-D-ribofuranosylamine p-toluenesulfonate salt (501 mg, 1.39 mmol) in 5 mL of N,N-dimethylformamide at room temperature was treated first with triethylamine (0.439 mL, 3.15 mmol) followed by the slow addition of 2-chloro-3-nitropyridine (200 mg, 1.26 mmol). After stirring at 50° C. for 48 h, the solution was diluted with ethyl acetate (15 mL) and washed with water (15 mL). The aqueous phase was further extracted with 15 mL of ethyl acetate and the combined organic extracts were dried over MgSO$_4$, filtered and concentrated in vacuo. The resulting crude product was purified by silica gel chromatography (4:1 to 1:1 hexane/ethyl acetate) to give the product which was deprotected following the procedure listed above for Acetonide Deprotection Step to give the crude product which was triturated with ether to give 3-nitro-2-(β-D-ribofuranosylamino)pyridine, 11 mg as a yellow solid.

5.1.5. Synthesis of 5-NITRO-2-(β-D-RIBOFURANOSYL-AMINO)PYRIDINE (5)

A solution of 2',3'-O-isopropylidene-β-D-ribofuranosylamine p-toluenesulfonate salt (501 mg, 1.39 mmol) in 5 mL of N,N-methylformamide at room temperature was treated first with triethylamine (0.439 mL, 3.15 mmol) followed by the slow addition of 2-chloro-5-nitropyridine (200 mg, 1.26 mmol). After stirring at 50° C. for 48 h, the solution was diluted with ethyl acetate (15 mL) and washed with water (15 mL). The aqueous phase was further extracted with 15 mL of ethyl acetate and the combined organic extracts were dried over MgSO$_4$, filtered and concentrated in vacuo. The resulting crude product was purified by silica gel chromatography (4:1 to 1:1 hexane/ethyl acetate) to give the product which was deprotected following the procedure listed above for Acetonide Deprotection Step to give the crude product which was triturated with ether to give 5-nitro-4-(β-D-ribofuranosylamino)pyridine, 43 mg.

5.1.6. Synthesis of (1R,2S,3R,5R-3-(6-AMINO-5-NITRO-PYRIMIDIN-4-YLAMINO)-5-HYDROXYMETHYL-CYCLOPENTANE-1,2-DIOL (6)

To a solution of 4-amino-6-chloro-5-nitropyrimidine (320 mg, 1.83 mmol) in N,N-dimethyl formamide (5 mL) and triethylamine (512 μL, 3.67 mmol) was added (1R,2S,3R, 5R)-3-Amino-5-hydroxymethyl-cyclopentane-1,2-diol (293 mg, 2.02 mmol). The mixture was stirred at room temperature and monitored by thin layer chromatography until starting material was no longer detected. The reaction mixture was diluted with water (20 mL) and extracted with diethyl ether (2×10 mL). The organic extract was washed with saturated aqueous sodium chloride (20 mL), dried over MgSO$_4$, filtered and concentrated in vacuo to give the crude product. The product was recrystallized from hot methanol/water to give a 298 mg of (1R,2S,3R,5R-3-(6-amino-5-nitro-pyrimidin-4-ylamino)-5-hydroxymethyl-cyclopentane-1,2-diol as a yellow solid.

5.1.7. Synthesis of (1S,2R,3S,5S)-3-(6-AMINO-5-NITRO-PYRIMIDIN-4-YLAMINO)-5-HYDROXYMETHYL-CYCLOPENTANE-1,2-DIOL (7)

To a solution of 4-amino-6-chloro-5-nitropyrimidine (320 mg, 1.83 mmol) in N,N-dimethyl formamide (5 mL) and triethylamine (512 μL, 3.67 mmol) was added (1S,2R,3S,5S-3-Amino-5-hydroxymethyl-cyclopentane-1,2-diol (293 mg, 2.02 mmol). The mixture was stirred at room temperature and monitored by thin layer chromatography until starting material was no longer detected The reaction mixture was diluted with water (20 mL) and extracted with diethyl ether (2×10 mL). The organic extract was washed with saturated aqueous sodium chloride (20 mL), dried over MgSO$_4$, filtered and concentrated in vacuo to give the crude product. The product was recrystallized from hot methanol/water to give a 315 mg of (1S,2R,3S,5S)-3-amino-5-nitro-pyrimidinylamino)-5-hydroxymethyl-cyclopentane-1,2-diol as a yellow solid.

5.1.8. Synthesis of 6-METHOXY-3-NITRO-2-(β-D-RIBOFURANOSYLAMINO)PYRIDINE (8)

A solution of 2',3'-O-Isopropylidene-D-ribofuranosylamine p-toluenesulfonate salt (422 mg, 1.17 mmol) in 5 mL of N,N-dimethylformamide at room temperature was treated first with triethylamine (0.369 mL, 2.65 mmol) followed by the slow addition of 2-chloro-6-methoxy-3-nitropyridine (200 mg, 1.06 mmol). After stirring at 50° C. for 48 h, the solution was diluted with ethyl acetate (15 mL) and washed with water (15 mL). The aqueous phase was further extracted with 15 mL of ethyl acetate and the combined organic extracts were dried over MgSO$_4$, filtered and concentrated in vacuo. The resulting crude product was purified by silica gel chromatography (3:1 to 1:1 hexane/ethyl acetate) to give the product which was deprotected following the procedure listed above for Acetonide Deprotection Step to give the crude product which was triturated with ether to give 6-methoxy-3-nitro-2-(β-D-ribofuranosylamino)pyridine, 41 mg as a brown oil.

5.1.9. Synthesis of 6-(DIMETHYLAMINO)-5-NITRO-4-(β-D-RIBOFURANOSYLAMINO)PYRIMIDINE (9)

To a solution of 6-chloro-5-nitro-4-(2',3'-O-isopropylidene-β-D-ribofuranosylamino)pyrimidine (121 mg, 0.349 mmol) in N,N-dimethylformamide (5 mL) at room temperature was added a 2.0M solution of dimethylamine in andhydrous tetrahydrofuran (698 μL, 1.4 mmol). The solution was stirred for 17 h, diluted with 15 mL ethyl acetate and washed with water. The aqueous layer was re-extracted with 10 mL ethyl acetate. The organic extracts were combined, washed with saturated aqueous sodium chloride (2×15 mL), dried over MgSO$_4$, filtered and concentrated in vacuo. The resulting crude product was purified by silica gel chromatography (3:1 hexane/ethyl acetate) to yield 88 mg of the product which was deprotected following the procedure listed above for Acetonide Deprotection Step to give 6-(dimethylamino)-5-nitro-4-(β-D-ribofuranosylamino)pyrimidine.

5.1.10. Synthesis of 6-(THIOMETHYL)-5-NITRO-4-(β-D-RIBOFURANOSYLAMINO)PYRIMIDINE (10)

To a solution of 6-chloro-5-nitro-4-(2',3'-O-isopropylidene-β-D-ribofuranosylamino)pyrimidine (200 mg, 0.577 mmol) in N,N-diethylformamide (2 mL) at room temperature was added sodium thiomethoxide (44 mg, 0.634 mmol). The solution was stirred for 5 h, diluted with 15 mL water and extracted with ethyl acetate (2×15 ml) and the combined organic layers were washed with brine (2×15 mL), dried over MgSO$_4$, filtered and concentrated in vacuo. The resulting 213 mg of yellow solid product was deprotected following the procedure listed above for Acetonide Deprotection Step to give crude product which was triturated with ether to afford 100 mg of 6-(thiomethyl)-5-nitro-4-(β-D-ribofuranosylamino)pyrimidine as a yellow solid.

5.1.11. Synthesis of 5-NITRO-4-METHYL-2-(β-D-RIBOFURANOSYLAMINO)PYRIDINE (11)

A solution of 2',3'-O-Isopropylidene-β-D-ribofuranosylamine p-toluenesulfonate salt (461 mg, 1.27 mmol) in 5 mL of N,N-dimethylformamide at room temperature was treated first with triethylamine (0.404 mL, 2.90 mmol) followed by the slow addition of 2-chloromethyl-5-nitropyridine (200 mg, 1.16 mmol). After stirring at 50° C. for 48 h, the solution was diluted with ethyl acetate (15 mL) and washed with water (15 mL). The aqueous phase was further extracted with 15 mL of ethyl acetate and the combined organic extracts were dried over MgSO$_4$, filtered and concentrated in vacuo. The resulting crude product was purified by silica gel chromatography (3:1 to 1:1 hexane/ethyl acetate) to give the product which was deprotected following the procedure listed above for Acetonide Deprotection Step to give the crude product which was triturated with ether to give 5-nitro-4-methyl-2-(6-D-ribofuranosylamino)pyridine, 26 mg as a brown oil. MS: M+1 286.

5.1.12. Synthesis of 6-AMINO-5-NITRO-4-(2',3'-O-ISOPROPYLIDENE-β-D-RIBOFURANOSYLAMINO)-RYRIMIDINE (12)

A solution of 2',3'-O-Isopropylidene-β-D-ribofuranosylamine p-toluenesulfonate salt (1.03 g, 2.85 mmol) in 10 mL of N,N-dimethylformamide at room temperature was treated first with triethylamine (0.662 mL, 4.75 mmol) followed by the slow addition of 6-chloro-5-nitro-pyrimidin-4-ylamine (331 mg, 1.90 mmol). After stirring at 50° C. for 48 h, the solution was diluted with ethyl acetate (30 mL) and washed with water (30 mL). The aqueous phase was further extracted with 20 mL of ethyl acetate and the combined organic extracts were washed with water (30 mL), brine (20 mL), dried over MgSO$_4$, filtered and concentrated in vacuo. The resulting crude product was purified by HPLC to give 6-amino-5-nitro-4-(2',3'-O-isopropylidene-β-D-ribofuranosylamino)pyrimidine.

5.1.13. Synthesis of 6-(2-HYDROXY-ETHYLAMINO)-5-NITRO-4-(β-D-RIBOFURANOSYLAMINO)PYRIMIDINE (13)

To a solution of 6-chloro-5-nitro-4-(2',3'-O-isopropylidene-β-D-ribofuranosylamino)pyrimidine (200 mg, 0.577 mmol) in N,N-dimethylformamide (10 mL) at room temperature was added ethanolamine (70 μL, 1.15 mmol). The solution was stirred for 17 h, diluted with 15 mL water and extracted with ethyl acetate (2×15 mL) and the combined organic layers were washed with brine (2×15 mL), dried over MgSO$_4$, filtered and concentrated in vacuo. The crude product was purified by preparative thin layer chromatography (3:1 ethyl acetate/hexanes) to give the product as a yellow oil. The product was deprotected following the procedure listed above for Acetonide Deprotection Step to give crude product which was triturated with ether to afford 6-(2-hydroxy-ethylamino)-5-nitro-4-(β-D-ribo-furanosylamino)pyrimidine.

5.1.14. Synthesis of 6-(ETHYLAMINO)-5-NITRO-4-(β-D-RIBO-FURANOSYLAMINO)PYRIMIDINE (14)

To a solution of 6-chloro-5-nitro-4-(2',3'-O-isopropylidene-β-D-ribofuranosylamino)pyrimidine (200 mg, 0.577 mmol) in N,N-dimethylformamide (5 mL) and triethylamine (201 μL, 1.44 mmol) at room temperature was added diethylamine hydrochloride (52 mg, 0.634 mmol). The solution was stirred for 2 h, diluted with 20 mL water and extracted with ethyl acetate (2×15 mL) and the combined organic layers were washed with 20 mL of brine, dried over MgSO$_4$, filtered and concentrated in vacuo. The resulting crude product was purified by silica gel chromatography (3:1 to 1:1 hexane/ethyl acetate) to afford 160 mg of product. The product was deprotected following the procedure listed above for Acetonide Deprotection Step to give 76 mg of 6-(ethylamino)-5-nitro-4-(β-D-ribo-furanosylamino)pyrimidine as a yellow solid.

5.1.15. Synthesis of 6-(4-METHOXY-BENZYLAMINO)-5-CYANO-4-(β-D-RIBOFURANOSYLAMINO)PYRIMIDINE (15)

A solution of 2',3'-O-Isopropylidene-β-D-ribofuranosylamine p-toluenesulfonate salt (158 mg, 0.437 mmol) in 5 mL of N,N-dimethylformamide at room temperature was treated first with triethylamine (0.127 mL, 0.910 mmol) followed by slow addition of(6-Chloro-5-nitro-pyrimidinyl)(4-methoxybenzyl)-amine (100 mg, 0.364 mmol). After stirring at 70° C. for 48 h, the solution was diluted with ethyl acetate (15 mL) and washed with water (15 mL). The aqueous phase was further extracted with ethyl acetate (10 mL) and the combined organic extracts were washed with water (15 mL), brine (10 mL), dried over MgSO$_4$, filtered and concentrated in vacuo. The resulting crude product was purified by preparative thin layer chromatography to give the product. The product was deprotected following the procedure listed above for Acetonide Deprotection Step to give 6-(4-methoxy-benzylamino)-5-cyano-4-(β-D-ribo-furanosylamino)pyrimidine 8 mg.

5.1.16. Synthesis of 3-CYANO-2-(β-D-RIBOFURANOSYL-AMINO)PYRIDINE (16)

A solution of 2',3'-O-Isopropylidene-β-D-ribofuranosylamine p-toluenesulfonate salt (1.435 g, 3.97 mmol) in 20 mL of t-butyl alcohol at room temperature was treated first with potassium t-butoxide (810 mg, 7.22 mmol) followed by the slow addition of 2-chloro-3-cyano-pyridine (500 mg, 3.61 mmol). After stirring at 50° C. for 17 h, the reaction mixture was concentrated in vacuo and diluted with ethyl acetate (20 mL) and washed with water (20 mL). The aqueous phase was further extracted with ethyl acetate (20 mL) and the combined organic extracts were washed with brine (20 mL), dried over MgSO$_4$, filtered and concentrated in vacuo. The resulting crude product was purified by silica gel chromatography (3:1 to 1:1 hexanes/ethyl acetate) to give 420 mg of product. The product was deprotected following the procedure listed above for Acetonide Deprotection Step to give 3-cyano-2-(β-D-ribofuranosyl-amino)pyridine.

5.1.17. Synthesis of 6-HYDROXY-5-NITRO-4-(β-D-RIBOFURANOSYLAMINO-2,3,5-TRIBENZOYL)PYRIMIDINE (17)

To a suspension of 6-amino-4-hydroxy-5-nitropyrimidine (1.25 g, 8.01 mmol) in anhydrous hexamethyldisilazane (37.5 mL) was added pyridine (6 mL), H$_2$SO$_4$ (0.25 mL), and (NH$_4$)$_2$SO$_4$ (0.040 g). The reaction mixture was heated at reflux for 17 h at which time the suspension gave way to a homogeneous solution. The reaction mixture was cooled and concentrated in vacuo to give a solid which was dissolved in anhydrous acetonitrile (63 mL) and stirred at room temperature while β-D-ribofuranose 1-acetate 2,3,5-tribenzoate (4.85 g, 9.61 mmol) was added followed by trimethylsilyl trifluoromethanesulfonate (2.50 mL, 12.5 mmol). The reaction mixture was stirred at room temperature for 4.5 h, then concentrated to give a viscous oil which was dissolved in methylene chloride (40 mL), washed with saturated aqueous NaHCO$_3$, dried over MgSO$_4$, filtered and concentrated. The crude product was purified by silica gel chromatography (1-5% acetone/methylene chloride) to give 4.03 g of 6-hydroxy-5-nitro-4-(β-D-ribofuranosyl-amino-2,3,5-tribenzoyl)pyrimidine as a glassy solid.

To a solution of 6-hydroxy-5-nitro-4-(β-D-ribofuranosyl-amino-2,3,5-tribenzoyl)pyrimidine (2.10 g, 3.50 mmol) in absolute methanol (83 mL) and anhydrous dioxane (16.6 mL) cooled in an ice bath was added 0.5 N sodium methoxide in methanol (1.4 mL, 0.7 mmol). The reaction was stirred in the ice bath for 1 hour, then sufficient Dowex 50WX4-50 resin was added to give a pH of 6. The resin was filtered, washed with methanol and discarded. The filtrate was concentrated and the crude product triturated with ethyl ether (5×4 mL) to give 1.00 g of 6-hydroxy-5-nitro-(β-D-ribofuranosylamino) pyrimidine.

5.1.18. Synthesis of 6-O-5-NITRO-4-(β-D-XYLOFURA-NOSYL-AMINO-2,3,5-TRIBENZOYL)PYRIMIDINE (18)

To a suspension of 4,6-diamino-5-nitropyrimidine (203 mg, 1.31 mmol) in anhydrous hexamethyldisilazane (5.9 mL) was added pyridine (0.95 mL), H$_2$SO$_4$ (40 μL), and (NH)SO$_4$ (6.7 mg). The reaction mixture was heated at reflux for 5 h at which time the suspension gave way to a homogeneous solution. The reaction mixture was cooled and concentrated in vacuo to give a solid which was dissolved in anhydrous acetonitrile (10 mL) and stirred at room temperature while β-D-xylofuranose 1,2,3,5-tetrabenzoate (0.60 g, 1.06 mmol) was added followed by trimethylsilyl trifluoromethanesulfonate (0.40 mL, 2.2 mmol). The reaction mixture was stirred at room temperature for 17 h and concentrated to give a viscous oil which was dissolved in methylene chloride (30 mL), washed with saturated aqueous NaHCO$_3$, dried over MgSO$_4$, filtered and concentrated. The crude product was purified by silica gel chromatography (1-10% acetonitrile/methylene chloride) to give 111 mg of 6-amino-5-nitro-4-(β-D-xylofuranosylamino-2,3,5-tribenzoyl)pyrimidine as a light yellow glassy solid.

To a solution of 6-amino-5-nitro-4-(β-D-xylofuranosylamino-2,3,5-tribenzoyl)pyrimidine (111 mg, 0.185 mmol) in absolute methanol (2.36 mL) and anhydrous dioxane (0.92 mL) cooled in an ice bath was added 0.5 N sodium methoxide in methanol (76 μL, 0.152 mmol). The reaction was stirred in the ice bath for 17 hours, then sufficient Dowex 50WX4-50 resin was added to give a pH of 6.5. The resin was filtered, washed with methanol and discarded. The filtrate was concentrated and the crude product triturated with ethyl ether (6×1.5 mL) to give 29 mg of crude product which was purified by silica gel chromatography (35% tetrahydrofuran/hexanes to 100% tetrahydrofuran) to give 15 mg of 6-amino-5-nitro-4-(β-D-xylofuranosylamino)pyrimidine.

5.1.19. Synthesis of 6-AMINO-5-NITRO-4-(β-L-RIBO-FURANOSYL-AMINO)PYRIMIDINE (19)

To a suspension of 4,6-diamino-5-nitropyrimidine (260 mg, 1.68 mmol) in anhydrous hexamethyldisilazane (7.8 mL) was added pyridine (1.3 mL), H$_2$SO$_4$ (0.52 μL), and (NH$_4$)$_2$SO$_4$ (12.3 mg). The reaction mixture was heated at reflux for 15 h at which time the suspension gave way to a homogeneous solution. The reaction mixture was cooled and concentrated in vacuo to give a solid which was dissolved in anhydrous acetonitrile (13 mL) and stirred at room temperature while β-L-ribofuranose 1-acetate 2,3,5-tribenzoate (1.00 g, 1.98 mmol) was added followed by trimethylsilyl trifluoromethanesulfonate (0.6 mL, 3 mmol). The reaction mixture was stirred at room temperature for 17 h, then concentrated to give a crude product which was dissolved in methylene chloride (20 mL), washed with saturated aqueous NaHCO$_3$, dried over MgSO$_4$, filtered and concentrated. The crude product was purified by silica gel chromatography (1-15% acetonitrile/methylene chloride) to give 0.77 g of 6-amino-5-nitro-4-(β-L-ribofuranosyl-amino-2,3,5-tribenzoyl)pyrimidine as a light yellow glassy solid.

To a solution of 6-amino-5-nitro-4-(β-L-ribofuranosyl-amino-2,3,5-tribenzoyl)pyrimidine (736 mg, 1.23 mmol) in absolute methanol (29 mL) and anhydrous dioxane (5.8 mL) cooled in an ice bath was added 0.5 N sodium methoxide in methanol (0.49 mL, 0.245 mmol). The reaction was stirred at 4° C. for 48 hours, then sufficient Dowex 50WX4-50 resin was added to give a pH of 6.5. The resin was filtered, washed with methanol and discarded. The filtrate was concentrated and the crude product triturated with ethyl ether (6×1.5 mL) to give 0.39 g of crude product which was purified by silica gel chromatography (35% tetrahydrofuran/hexanes to 100% tetrahydrofuran) to give 237 mg of 6-amino-5-nitro-4-(β-L-ribofuranosyl-amino)pyrimidine.

5.1.20. Synthesis of 6-AMINO-5-NITRO-4-(5-DEOXY-5-FLUORO-β-D-RIBOFURANOSYLAMINO)-PYRI-DINE (20)

To a suspension of 4,6-diamino-5-nitropyrimidine (1.32 g, 8.51 mmol) in anhydrous hexamethyldisilazane (40 mL) was added pyridine (6.3 mL), H$_2$SO$_4$ (260 μL), and (NH$_4$)SO$_4$ (40 mg). The reaction mixture was heated at reflux for 15 h at which time the suspension gave way to a homogeneous solution. The reaction mixture was cooled and concentrated in vacuo to give a solid which was dissolved in anhydrous acetonitrile (63 mL) and stirred at room temperature while β-D-ribofuranose 5-t-butyldiphenylsilyloxy-1,2,3-tribenzoate (5.92 g, 8.45 mmol) was added followed by trimethylsilyl trifluoromethanesulfonate (2.2 mL, 12.2 mmol). The reaction mixture was stirred at room temperature for 30 min, then quenched by addition of saturated aqueous NaHCO$_3$ (15 mL) and stirred overnight. The mixture was filtered through celite to remove suspended solids and the filtrate was extracted with methylene chloride (3×15 mL). The extract was washed with water, dried over MgSO$_4$, filtered and concentrated. The crude product was purified by silica gel chromatography (1-6% acetonitrile/methylene chloride) to give 3.85 g of 6-amino-5-nitro-4-(β-D-ribofuranose 5-t-butyldiphenylsilyloxy-1,2,-dibenzoyl)pyrimidine.

To a solution of 6-amino-5-nitro-4-(β-D-ribofuranosyl-5-t-butyldiphenylsilyloxy-1,2-dibenzoyl)pyrimidine (2.67 g, 3.64 mmol) in anhydrous tetrahydrofuran (18 mL) was added a 1 M solution of tetra-n-butylammonium fluoride in tetrahydrofuran (4.0 ml, 4.0 mmol). After 30 minutes water (10 mL) was added and the mixture was concentrated to remove tetrahydrofuran. The aqueous mixture was extracted with ethyl acetate (5×4 mL). The combined extract was concentrated and purified by silica gel chromatography (5% to 40% acetonitrile/methylene chloride) to give 1.67 g of 6-amino-5-nitro-4-(β-D-ribofuranose-1,2-dibenzoate)pyrimidine as a glassy solid.

To a solution of 6-amino-5-nitro-4-(β-D-ribofuranosy-lamino-2,3-dibenzoyl)pyrimidine (205 mg, 0.414 mmol) in anhydrous methylene chloride (4 mL) was added diethylaminosulfurtrifluoride (60 μL, 0.46 mmol). The mixture was stirred at room temperature for 48 hours then washed with saturated aqueous sodium bicarbonate (10 mL), dried over $MgSO_4$ and concentrated to give 192 mg of crude product which was purified by silica gel chromatography to give 85 mg of 6-amino-5-nitro-4-(β-D-5-deoxy-5-fluoro-2,3-dibenzoylribofuranosylamino)pyrimidine.

To a solution of 6-amino-5-nitro-4-(β-D-5-deoxy-5-fluoro-2,3-dibenzoyl ribofuranosylamino)pyrimidine (77 mg, 0.155 mmol) in absolute methanol (3.7 mL) and anhydrous dioxane (0.73 mL) cooled in an ice bath was added 0.5 N sodium methoxide in methanol (75 μL, 0.0375 mmol). The reaction was stirred at 0° C. for 6 hours, then sufficient Dowex 50WX4-50 resin was added to give a pH of 6. The resin was filtered, washed with methanol and discarded The filtrate was concentrated and the crude product was purified by silica gel chromatography (1-10% methanol/methylene chloride) to give 17 mg of 6-amino-5-nitro-4-(5-deoxy-5-fluoro-β-D-ribofuranosylamino)-pyrimidine.

5.1.21. Synthesis of 6-AMINO-5-NITRO-4-(5-DEOXY-5-AZIDO-β-D-RIBOFURANOSYLAMINO)-PYRIMIDINE (21)

To a solution of 6-amino-5-nitro-4-(β-D-ribofuranosylamino-2,3-dibenzoyl)pyrimidine (248 mg) in anhydrous methylene chloride (2.50 mL) was added triethylamine (140 μL, 1.00 mmol) at 0° C. Methanesulfonyl chloride (43 μL, 0.56 mmol) was added and the mixture was stirred overnight at 0° C. The reaction mixture was washed with water (10 mL) dried over $Na_2SO_4$, filtered and concentrated to give 289 mg of 6-amino-5-nitro-4-(β-D-ribofuranosylamino-5-methanesulfonyloxy-2,3-dibenzoyl)pyrimidine.

To a solution of 6-amino-5-nitro-4-(β-D-ribofuranosylamino-5-methanesulfonyloxy-2,3-dibenzoyl)pyrimidine (271 mg, 0.473 mmol) in N,N-dimethylformamide (1 mL) was added sodium azide (46.2 mg, 0.71 mmol). The mixture was heated to 100° C. for 7 hours, then diluted with water to give a precipitate. The precipitate was filtered, washed with water and dried to give 230 mg of 6-amino-5-nitro-4-(β-D-ribofuranosylamino-5-deoxy-5-azido-2,3-dibenzoyl)pyrimidine.

To a solution of 6-amino-5-nitro-4-(β-D-ribofuranosylamino-5-deoxy-5-azido-2,3-dibenzoyl)pyrimidine (199 mg, 0.382 mmol) in absolute methanol (9 mL) and anhydrous dioxane (1.8 mL) cooled in an ice bath was added 0.5 N sodium methoxide in methanol (152 μL, 0.076 mmol). The reaction was stirred at 0° C. for 17 hours, then sufficient Dowex 50WX4-50 resin was added to give a pH of 6. The resin was filtered, washed with methanol and discarded. The filtrate was concentrated and the crude product was purified by silica gel chromatography (5-25% dioxane/methylene chloride) to give 70 mg of 6-amino-5-nitro-4-(β-D-5-deoxy-5-azidoribofuranosylamino)pyrimidine.

5.1.22. Synthesis of 6-AMINO-5-NITRO-4-(α-D-RIBOFURANOSYLAMINO)-PYRIMIDINE (22)

A solution of 2',3'-O-Isopropylidene-β-D-ribofuranosylamine p-toluenesulfonate salt (10.83 g, 30 mmol) in 60 mL of acetonitrile was stirred at room temperature with sodium sulfate (15 g) for 1 hour. 4,6-dichloro-5-nitropyrimidine (11.64 g, 60 mmol) was added followed by diisopropylethylamine (5.97 g, 45 mmol). The reaction mixture was stirred at room temperature for 30 h. The sodium sulfate was removed by filtration and the filtrate was concentrated to give an oil. The crude product was purified using silica gel chromatography (1:3 to 1:1 ethyl acetate/hexanes) to give 6-chloro-5-nitro-4-(2',3'-O-isopropylidene-α-D-ribofuranosylamino) pyrimidine, 1.41 g.

A solution 6-chloro-5-nitro-4(2',3'-O-isopropylidene-α-D-ribofuranosylamino)pyrimidine (1.41 g, 4 mmol) in andhydrous dioxane (25 mL) was stirred at 0° C. as a solution of 7 M ammonia in methanol (5 mL, 35 mmol) was added. The mixture was stirred overnight at 0° C. then filtered to remove a solid. The filtrate was concentrated and purified by silica gel chromatography (5% methanol in methylene chloride) to give 1.32 g of 6-amino-5-nitro-4-(2',3'-O-isopropylidene-α-D-ribofuranosylamino)pyrimidine.

A solution of 98% aqueous trifluoroacetic acid was added to 6-amino-5-nitro-4-(2',3'-O-isopropylidene-α-D-ribofuranosylamino)pyrimidine (200 mg, 0.611 mmol) at room temperature. The reaction mixture was stirred for 1 hour at room temperature then concentrated. The product was purified by HPLC to give 6-Amino-5-nitro-4-(α-D-ribofuranosylamino) pyrimidine 64 mg.

5.1.23. Synthesis of 6-AMINO-5-NITRO-4-[(5-O-ACETYL-β-D-RIBOFURANOSYL)AMINO]PYRIMIDINE (23)

To a solution of 6-amino-5-nitro-4(2',3'-O-isopropylidene-β-D-ribofuranosylamino)pyrimidine (200 mg, 0.611 mmol) in anhydrous tetrahydrofuran (3 mL) stirring at room temperature was added triphenylphosphine (240 mg, 0.917 mmol) and acetic acid (0.05 mL, 0.92 mmol). The reaction mixture was cooled in a −25° C. bath and a solution of diethyl azodicarboxylate (160 mg, 0.917 mmol) in andhydrous tetrahydrofuran (1 mL) was added over 10 minutes. The mixture was stirred at −25° C. for 20 minutes after addition, then allowed to warm to room temperature. The reaction mixture was diluted with saturated aqueous sodium bicarbonate and extracted with methylene chloride. The combined organic extracts were concentrated and purifed by silica gel chromatography (methylene chloride then 1% methanol/methylene chloride) to give 103.5 mg of 6-amino-5-nitro-4-[(2,3-O-isopropylidene-5-O-acetyl-β-D-ribofuranosyl)amino]pyrimidine.

To acetic acid 6-Amino-5-nitr[(2,3-O-isopropylidene-5-O-acetyl-β-D-ribofuranosyl)amino]pyrimidine (103.5 mg, 0.280 mmol) was added 98% aqueous trifluoroacetic acid at −25° C. The mixture was stirred for 20 minutes, then concentrated to give acetic acid 6-Amino-5-nitro-4-[(5-O-acetyl-β-D-ribofuranosyl)amino]pyrimidine.

5.1.24. Synthesis of 6-AMINO-5-NITRO-4-[(2,3,5-TRI-O-BENZOYL-β-D-RIBOFURANOSYL)AMINO]PYRIMIDINE (24)

To a suspension of 4,6-diamino-5-nitropyrimidine (1.25 g, 8.05 mmol) in anhydrous hexamethyldisilazane (37.5 mL) was added pyridine (6 mL), $H_2SO_4$ (0.25 mL) and $(NH_4)_2SO_4$ (0.040 g). The reaction mixture was heated at reflux for 1.5 h at which time the suspension gave way to a homogeneous solution. The reaction mixture was cooled and concentrated in vacuo to give a solid which was dissolved in anhydrous acetonitrile (63 mL) and stirred at room temperature as β-D-ribofuranose 1-acetate 2,3,5-tribenzoate (4.85 g, 9.61 mmol) was added followed by trimethylsilyl trifluoromethanesulfonate (2.50 mL, 12.5 mmol). The reaction mixture was stirred at room temperature for 4.5 h, then concentrated to give a viscous oil which was dissolved in methylene chloride (40 mL), washed with saturated aqueous $NaHCO_3$, dried over $MgSO_4$, filtered and concentrated. The crude product was purified by silica gel chromatography (1-10% acetonitrile/methylene chloride) to give 1.84 g of 6-amino-5-nitro-4-(β-D-ribofuranosyl-amino-2,3,5-tribenzoyl)pyrimidine as a light yellow glassy solid.

5.1.25. Synthesis of METHYL 6-CHLORO-4-(β-D-RIBOFURANOSYLAMINO)PYRIMIDINE-5-CARBOXY- LATE (25) and METHYL 6-CHLORO-4-(α-D-RIBO-FURANOSYLAMINO)PYRIMIDINE-5-CARBOXYLATE (26)

A solution of 2',3'-O-Isopropylidene-β-D-ribofuranosylamine p-toluenesulfonate salt (3.80 g, 11 mmol) in 50 mL of N,N-methylformamide at room temperature was treated first with methyl 4,6-dichloropyrimidyl-5-carboxylate (1.9 g, 9.2 mmol) followed by the slow addition of diisopropylethylamine (5 mL, 27.5 mmol). The mixture was stirred for 18 hours at room temperature and then concentrated. The crude product was purified by silica gel chromatography (50% ethyl acetate/hexanes to 100% ethyl acetate) to give 1.05 g of 6-chloro-4-[2',3'-O-isopropylidene-β-D-ribofuranosyl)amino]pyrimidine-5-carboxylate and 0.32 g of methyl 6-chloro-4-[2',3'-O-isopropylidene-α-D-ribofuranosyl)amino]pyrimidine-5-carboxylate.

Methyl 6-chloro[2',3'-O-isopropylidene-β-D-ribofuranosyl)amino]pyrimidine-5-carboxylate was treated with 90% aqueous trifluoroacetic acid (8 mL) at room temperature for 6 minutes then concentrated to give the crude product which was co-evaporated with water (3×3 mL) and then treated with dichloromethane (5 mL) and acetone (5 mL). The resulting precipitate was filtered and dried under high vacuum to give methyl 6-chloro-4-(β-D-ribofuranosylamino)pyrimidine-5-carboxylate, 66 mg as a white solid.

Treatment of methyl 6-chloro-4-[2',3'-O-isopropylidene-α-D-ribofuranosyl)amino]pyrimidine-5-carboxylate (80 mg, 0.22 mmol) in the same manner gave methyl 6-chloro-4-(α-D-ribofuranosylamino)pyrimidine-5-carboxylate 30 mg as a solid.

5.1.26. Synthesis of METHYL 6-AMINO-4-(β-D-RIBOFURANOSYLAMINO)PYRIMIDINE-5-CARBOXYLATE (27) and METHYL 6-AMINO-4-(α-D-RIBOFURANOSYLAMINO)PYRIMIDINE 5-CARBOXYLATE (28)

A solution of methyl 6-chloro-4-[2',3'-O-isopropylidene-β-D-ribofuranosyl)amino]pyrimidine-5-carboxylate (0.4 g, 1.11 mmol) in 7 N ammonia in methanol (10 mL, 70 mmol) was stirred at room temperature for 18 hours and then concentrated. The crude product was purified by silica gel chromatography (90% acetonitrile/water to 100% acetonitrile) to give methyl 6-amino-4-[2',3'-O-isopropylidene-β-D-ribofuranosyl)amino]pyrimidine-5-carboxylate, 0.291 g.

A solution of methyl 6-amino-4-[2',3'-O-isopropylidene-β-D-ribofuranosyl)amino]pyrimidine-5-carboxylate (60 mg, 0.176 mmol) in 90% aqueous trifluoroacetic acid (4 mL) was stirred for 6 minutes at room temperature and then concentrated. The resulting gum was co-evaporated with water (3×3 mL) and then treated with dichloromethane (5 mL), acetone (5 mL) and hexanes (2 mL). The precipitate was filtered and dried to give methyl 6-amino-4-(β-D-ribofuranosylamino)pyrimidine-5-carboxylate 32 mg as an off-white solid.

The two step procedure used above was used to convert 168 mg of methyl 6-chloro-4-(2',3'-O-isopropylidene-α-D-ribofuranosyl)amino)pyrimidine-5-carboxylate into methyl 6-amino-4-(α-D-ribofuranosylamino)pyrimidine-5-carboxylate, 50 mg.

5.2 Example 2

Identification and Characterization of Compounds that Promote Nonsense Suppression and/or Modulate Translation Termination 5.2.1. Increase in In Vitro Nonsense Suppression at UGA Codons Compounds of the invention can be characterized further with the in vitro luciferase nonsense suppression assay. To ensure that the observed nonsense suppression activity of the selected compounds is not limited to the rabbit reticulocyte assay system, HeLa cell extract is prepared and optimized (Lie & Macdonald, 1999, Development 126(22):4989-4996 and Lie & Macdonald, 2000, Biochem. Biophys. Res. Commun. 270(2):473-481). The nonsense suppression activity of compounds of the invention, with respect to the UGA codon, are compared to gentamicin in the HeLa cell translation extracts.

5.2.2. Characterization of Compounds that Increase Nonsense Suppression AND Produce Functional Protein A stable cell line harboring the UGA nonsense-containing luciferase gene is treated with a test compound. Cells are grown in standard medium supplemented with 1% penicillin-streptomycin (P/S) and 10% fetal bovine serum (FBS) to 70% confluency and split 1:1 the day before treatment. The next day, cells are trypsinized and 40,000 cells are added to each well of a 96-well tissue culture dish. Serial dilutions of each compound are prepared to generate a six-point dose response curve spanning 2 logs (30 µM to 0.3 µM). The final concentration of the DMSO solvent remains constant at 1% in each well. Cells treated with 1% DMSO serve as the background standard, and cells treated with gentamicin serve as a positive control.

5.2.3. Alteration of the Accessibility of Chemical Modifying Agents to Specific Nucleotides in the 28S rRNA Previous studies have demonstrated that gentamicin and other members of the aminoglycoside family that decrease the fidelity of translation bind to the A site of the 16S rRNA. By chemical footprinting, UV cross-linking and NMR, gentamicin has been shown to bind at the A site (comprised of nucleotides 1400-1410 and 1490-1500, E. coli numbering) of the rRNA at nucleotides 1406, 1407, 1494, and 1496 (Moazed & Noller, Nature 327(6121):389-394 (1978); Woodcock et al., EMBO J. 10(10):3099-3103 (1991); and Schroeder et al., EMBO J. 19:1-9 (2000).

Ribosomes prepared from HeLa cells are incubated with the small molecules(at a concentration of 100 mM), followed by treatment with chemical modifying agents (dimethyl sulfate [DMS] and kethoxal [KE]). Following chemical modification, rRNA is phenol-chloroform extracted, ethanol precipitated, analyzed in primer extension reactions using end-labeled oligonucleotides hybridizing to different regions of the three rRNAs and resolved on 6% polyacrylamide gels. The probes used for primer extension cover the entire 18S (7 oligonucleotide primers), 28S (24 oligonucleotide primers), and 5S (one primer) rRNAs. Controls in these experiments include DMSO (a control for changes in rRNA accessibility induced by DMSO), paromomycin (a marker for 18S rRNA binding), and anisomycin (a marker for 28S rRNA binding).

5.2.4. Readthrough of Premature Termination Codons in Cell-Based Disease Models

To address the effects of the nonsense-suppressing compounds on mRNAs altered in specific inherited diseases, a bronchial epithelial cell line harboring a nonsense codon at amino acid 1282 (WI 282x) is treated with a compound of the invention and CFTR function is monitored as a cAMP-activated chloride channel using the SPQ assay (Yang et al., Hum. Mol. Genet. 2(8):1253-1261 (1993) and Howard et al., Nat. Med. 2(4):467-469(1996)). The increase in SPQ fluorescence in cells treated with a compound of the invention is compared to those treated with cAMP and untreated cells. An increase in SPQ fluorescence in cells is consistent with stimulation of CFTR-mediated halide efflux and an increase in readthrough of the nonsense codon. Full-length CFTR expression from this nonsense-containing allele following treatment with a compound of the invention demonstrates that cystic fibrosis cell lines increase chloride channel activity when treated with a compound of the invention.

5.2.5. Expression of Full Length Dystrophin Protein in the Nonsense Mutation-Containing MDX Mouse Cell by Treatment The mutation in the mdx mouse that premature termination of the 427 kDa dystrophin polypeptide has been shown to be a C to T transition at position 3185 in exon 23 (Sicinski et al., Science 244(4912):1578-1580(1989)). Mouse primary skeletal muscle cultures derived from 1-day old mdx mice are prepared as described previously carton-Davis et al., J. Clin. Invest. 104(4):375-381(1999)). Cells are cultured for 10 days in the presence of a compound of the invention. Culture medium is replaced every four days and the presence of dystrophin in myoblast cultures is detected by immunostaining as described previously (Barton-Davis et al., J. Clin. Invest. 104(4):375-381(1999)). A primary monoclonal antibody to the C-terminus of the dystrophin protein (F19A12) is used undiluted and rhodamine conjugated anti-mouse IgG was used as the secondary antibody. The F19A12 antibody detects the full-length protein produced by suppression of the nonsense codon. Staining is viewed using a Leica DMR microscope, digital camera, and associated imaging software at the University of Pennsylvania

5.2.6. Readthrough of Premature Termination Codons in the MDX

As previously described (Barton-Davis et al., J. Clin. Invest. 104(4):375-381(1999), compound is delivered by Alzet osmotic pumps implanted under the skin of anesthetized mice. Two doses of a compound of the invention are administered. Gentamicin serves as a positive control and pumps filled with solvent only serve as the negative control. Pumps are loaded with appropriate compound such that the calculated doses to which tissue is exposed are 10 mM and 20 mM. The gentamicin concentration is calculated to achieve tissue exposure of approximately 200 mM. In the initial experiment, mice are treated for 14 days, after which animals are anesthetized with ketamine and exsanguinated. The tibialis anterior (TA) muscle of the experimental animals is then excised, frozen, and used for immunofluorescence analysis of dystrophin incorporation into striated muscle. The presence of dystrophin in TA muscles is detected by immunostaining, as described previously (Barton-Davis et al., J. Clin. Invest. 104(4):375-381(1999).

5.3 Example 3

100 mg Oral Dosage Form

Table 3 illustrates a batch formulation and a single dose unit formulation containing 100 mg of clitocine.

TABLE 3

Formulation for 100 mg tablet

| Material | Percent by Weight | Quantity (mg/tablet) | Quantity (kg/batch) |
|---|---|---|---|
| 6-Amino-5-nitro-4-(β-D-ribo-furanosylamino) pyrimidine (Clitocine) | 40% | 100.00 | 20.00 |
| Microcrystalline Cellulose, NF | 53.5% | 133.75 | 26.75 |
| Pluronic F-68 Surfactant | 4.0% | 10.00 | 2.00 |
| Croscarmellose Sodium Type A, NF | 2.0% | 5.00 | 1.00 |
| Magnesium Stearate, NF | 0.5% | 1.25 | 0.25 |
| Total | 100.0% | 250.00 mg | 50.00 kg |

The microcrystalline cellulose, croscarmellose sodium, and clitocine are passed through a #30 mesh screen (about 430μ to about 655μ). The Pluronic F-68® (manufactured by JRH Biosciences, Inc. of Lenexa, Kans.) surfactant is passed through a #20 mesh screen (about 457μ to about 1041μ). The Pluronic F-689 surfactant and 0.5 kgs of croscarmellose sodium are loaded into a 16 qt. twin shell tumble blender and are mixed for about 5 minutes. The mix is then transferred to a 3 cubic foot twin shell tumble blender where the microcrystalline cellulose is added and blended for about 5 minutes. The thalidomide is added and blended for an additional 25 minutes. This pre-blend is passed through a roller compactor with a hammer mill attached at the discharge of the roller compactor and moved back to the tumble blender. The remaining croscarmellose sodium and magnesium stearate is added to the tumble blender and blended for about 3 minutes. The final mixture is compressed on a rotary tablet press with 250 mg per tablet (200,000 tablet batch size).

5.4 Example 4

Aerosol Dosage Form

A concentrate is prepared by combining clitocine and a 12.6 kg portion of the trichloromonofluoromethane in a sealed stainless steel vessel equipped with a high shear mixer. Mixing is carried out for about 20 minutes. The bulk suspension is then prepared in the sealed vessel by combining the concentrate with the balance of the propellants in a bulk product tank that is temperature controlled to 21° to 27° C. and pressure controlled to 2.8 to 4.0 BAR. 17 ml aerosol containers which have a metered valve which is designed to provide 100 inhalations of the composition of the invention. Each container is provided with the following:

| | |
|---|---|
| ipratropium bromide, 6-Amino-5-nitro-4-(β-D-ribofuranosylamino)pyrimidine | 0.0021 g |
| tetrahydro-furan-3,4-diol | 0.0120 g |
| trichloromonofluoromethane | 1.6939 g |
| dichlorodifluoromethane | 3.7028 g |
| dichlorotetrafluoroethane | 1.5766 g |
| total | 7.0000 g |

5.5 Example 5

Intravenous Dosage Form

The intravenous formulation is prepared by reconstituting clitocine with an appropriate liquid medium, such as water for injection (WFI) or a 5% dextrose solution. A desired concentration of the intravenous formulation can be obtained by reconstituting an appropriate amount of clitocine with an appropriate volume of liquid medium. A desired concentration of the intravenous formulation provides a therapeutically effective amount of clitocine to the patient, preferably a mammal, more preferably a human, in need of the intravenous pharmaceutical formulation and maintains a therapeutically effective level of clitocine in the patient. The dose which is therapeutically effective will depend on the rate at which the intravenous formulation is delivered to the patient and the concentration of the intravenous formulation. For example, two vials containing a composition (e.g., 500 mg of clitocine per vial) are reconstituted with a 5% dextrose solution (14 ml of 5% dextrose solution per vial) yielding a total of 28 mL of solution. The reconstituted solution is incorporated into a dextrose solution in an infusion bag and q.s. to 166 mL, resulting in a solution containing 6 mg/ml of clitocine suitable for intravenous infusion administration. The preferred concentration of clitocine in the liquid medium, in the infusion bag, is about 3 to about 10 mg/ml, preferably about 5 to about 6 mg/ml.

While the invention has been described with respect to the particular embodiments, it will be apparent to those skilled in the art that various changes and modifications may be made without departing from the spirit and scope of the invention as defined in the claims. Such modifications are also intended to fall within the scope of the appended claims.

What is claimed is:

1. A method of treating cystic fibrosis or muscular dystrophy responsive to modulation of premature translation termination and/or nonsense-mediated mRNA decay comprising administering to a patient in need thereof an effective amount of a compound having the structure of formula VII:

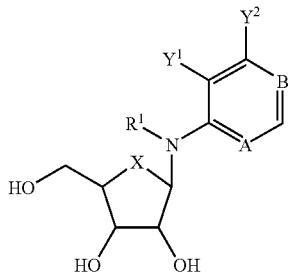

VII or a pharmaceutically acceptable salt, hydrate, solvate, clathrate, racemate or stereoisomer thereof, wherein:
   X is O;
   A and B are each independently CH or N, wherein CH is substituted or unsubstituted;
   $Y^1$ and $Y^2$ are each independently hydrogen, hydroxy, halogen, nitro, cyano, sulfate, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, alkoxy, alkylthioether, carboxyalkyl, carbonylalkyl, amino, $NR^5R^{5'}$, amido, or alkoxycarbonyl;
   $R^1$ is hydrogen, substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl; and
   $R^5$ and $R^{5'}$ are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl,
   wherein groups that are substituted are independently substituted with one or more substituents selected from the group consisting of alkyl, alkenyl, alkynyl, cycloalkyl, aroyl, halo, haloalkyl, haloalkoxy, hydroxy, alkoxy, alkylthioether, cycloalkyloxy, heterocylooxy, oxo, alkanoyl, aryl, arylalkyl, alkylaryl, heteroaryl, heteroarylalkyl, alkylheteroaryl, aryloxy, alkanoyloxy, amino, alkylamino, arylamino, arylalkylamino, cycloalkylamino, heterocycloamino, mono- or di-substituted amino, alkanoylamino, aroylamino, aralkanoylamino, alkanoylamino, arylamino, aralkanoylamino, thiol, alkylthio, arylthio, arylalkylthio, cycloalkylthio, heterocyclothio, alkylthiono, arylthiono, arylalkylthiono, alkylsulfonyl, arylsulfonyl, arylalkylsulfonyl, sulfonamido, nitro, cyano, carboxy, carbamyl, alkoxycarbonyl, guanidino or heterocycloalkyl.

2. The method of claim 1, wherein the compound, or a pharmaceutically acceptable salt, hydrate, solvate, clathrate or stereoisomer thereof, is administered as a composition comprising the compound and a pharmaceutically acceptable carrier or diluent.

3. The method claim 1, wherein A and B are each N or wherein A is N and B is substituted or unsubstituted CH.

4. The method of claim 1, wherein the compound has the structure of formula IX:

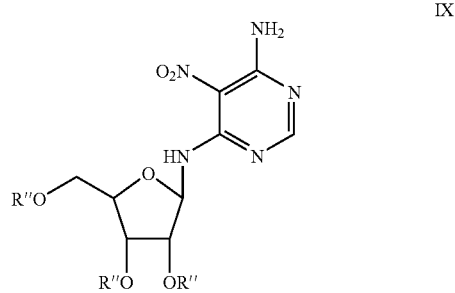

IX or a pharmaceutically acceptable salt, hydrate, solvate, clathrate, racemate or stereoisomer thereof, wherein each occurrence of R" is hydrogen.

5. A method of treating cystic fibrosis or muscular dystrophy associated with a genetic nonsense mutation comprising administering to a patient in need thereof an effective amount of a compound having the structure of formula VII:

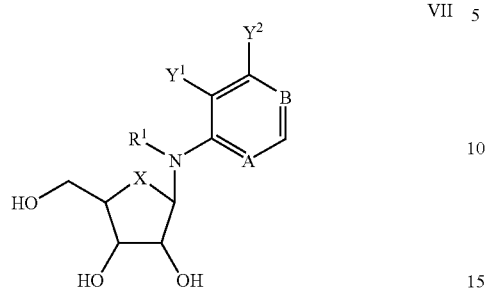

or a pharmaceutically acceptable salt, hydrate, solvate, clathrate, racemate or stereoisomer thereof, wherein:

X is O;

A and B are each independently CH or N;

$Y^1$ and $Y^2$ are each independently hydrogen, hydroxy, halogen, nitro, cyano, sulfate, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, alkoxy, alkylthioether, carboxyalkyl, carbonylalkyl, amino, $NR^5R^{5'}$, amido, or alkoxycarbonyl;

$R^1$ is hydrogen, substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl; and $R^5$ and $R^{5'}$ are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, wherein groups that are substituted are independently subsituted with one or more substituents selected from the group consisting of alkyl, alkenyl, alkynyl, cycloalkyl, aroyl, halo, haloalkyl, haloalkoxy, hydroxy, alkoxy, alkylthioether, cycloalkyloxy, heterocylooxy, oxo, alkanoyl, aryl, arylalkyl, alkylaryl, heteroaryl, heteroarylalkyl, alkylheteroaryl, aryloxy, alkanoyloxy, amino, alkylamino, arylamino, arylalkylamino, cycloalkylamino, heterocycloamino, mono- or di-substituted amino, alkanoylamino, aroylamino, aralkanoylamino, alkanoylamino, arylamino, aralkanoylamino, thiol, alkylthio, arylthio, arylalkylthio, cycloalkylthio, heterocyclothio, alkylthiono, arylthiono, arylalkylthiono, alkylsulfonyl, arylsulfonyl, arylalkylsulfonyl, sulfonamido, sulfonamido, nitro, cyano, carboxy, carbamyl, alkoxycarbonyl, guanidino or heterocycloalkyl.

6. A method of modulating premature translation termination and/or nonsense-mediated mRNA decay in a cell, comprising contacting a cell exhibiting premature translation termination and/or nonsense-mediated mRNA decay with an effective amount of a compound having the structure of formula VII:

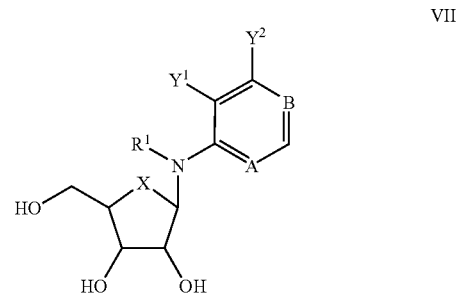

or a pharmaceutically acceptable salt, hydrate, solvate, clathrate, racemate or stereoisomer thereof, wherein:

X is O;

A and B are each independently CH or N;

$Y^1$ and $Y^2$ are each independently hydrogen, hydroxy, halogen, nitro, cyano, sulfate, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, alkoxy, alkylthioether, carboxyalkyl, carbonylalkyl, amino, $NR^5R^{5'}$, amido, or alkoxycarbonyl;

$R^1$ is hydrogen, substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl; and $R^5$ and $R^{5'}$ are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, wherein groups that are substituted are independently subsituted with one or more substituents selected from the group consisting of alkyl, alkenyl, alkynyl, cycloalkyl, aroyl, halo, haloalkyl, haloalkoxy, hydroxy, alkoxy, alkylthioether, cycloalkyloxy, heterocylooxy, oxo, alkanoyl, aryl, arylalkyl, alkylaryl, heteroaryl, heteroarylalkyl, alkylheteroaryl, aryloxy, alkanoyloxy, amino, alkylamino, arylamino, arylalkylamino, cycloalkylamino, heterocycloamino, mono- or di-substituted amino, alkanoylamino, aroylamino, aralkanoylamino, alkanoylamino, arylamino, aralkanoylamino, thiol, alkylthio, arylthio, arylalkylthio, cycloalkylthio, heterocyclothio, alkylthiono, arylthiono, arylalkylthiono, alkylsulfonyl, arylsulfonyl, arylalkylsulfonyl, sulfonamido, sulfonamido, nitro, cyano, carboxy, carbamyl, alkoxycarbonyl, guanidino or heterocycloalkyl.

7. A method of treating cystic fibrosis or muscular dystrophy associated with a genetic nonsense mutation comprising administering to a patient in need thereof a compound having the structure:

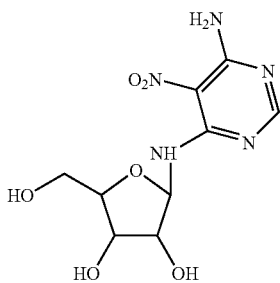

or a pharmaceutically acceptable salt, hydrate, solvate, clathrate, racemate or stereoisomer thereof.

8. The method of claim 1, wherein a pharmaceutically acceptable salt of a compound of formula VII is administered.

9. The method of claim 1, wherein a pharmaceutically acceptable hydrate or solvate of a compound of formula VII is administered.

10. The method of claim 5, wherein a pharmaceutically acceptable salt of the compound of claim 5 is administered.

11. The method of claim 5, wherein a pharmaceutically acceptable hydrate or solvate of the compound of claim 5 is administered.

12. The method of claim 6, wherein the cell is contacted with a pharmaceutically acceptable salt of the compound of claim 6.

13. The method of claim 6, wherein the cell is contacted with a pharmaceutically acceptable hydrate or solvate of the compound of claim 6.

14. The method of claim 7, wherein a pharmaceutically acceptable salt of the compound of claim 7 is administered.

15. The method of claim 7, wherein a pharmaceutically acceptable hydrate or solvate of the compound of claim 7 is administered.

16. The method of claim 1, wherein $R^1$ is hydrogen.

17. The method of claim 1, wherein $Y^1$ is hydrogen, halogen, hydroxy, nitro, —$NH^2$, —NH-alkyl, —NH-alkyl-OH, —$N(alkyl)^2$, —NH-alkyl-phenyl, sulfate, carboxy, alkoxycarbonyl, cyano, alkyl, alkylcarbonyl or alkylthio, wherein phenyl is substituted or unsubstituted with alkoxy.

18. The method of claim 1, wherein $Y^2$ is hydrogen, halogen, hydroxy, nitro, —$NH^2$, —NH-alkyl, —NH-alkyl-OH, —$N(alkyl)^2$, —NH-alkyl-phenyl, sulfate, carboxy, alkoxycarbonyl, cyano, alkyl, alkylcarbonyl or alkylthio, wherein phenyl is substituted or unsubstituted with alkoxy.

* * * * *